United States Patent
Osada et al.

(10) Patent No.: US 9,496,095 B2
(45) Date of Patent: Nov. 15, 2016

(54) COMPOUND AND CARRIER SYSTEM HAVING THE COMPOUND

(71) Applicant: ADEKA CORPORATION, Tokyo (JP)

(72) Inventors: Hiroyuki Osada, Tokyo (JP); Yohei Aoyama, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 373 days.

(21) Appl. No.: 14/372,462

(22) PCT Filed: Feb. 27, 2013

(86) PCT No.: PCT/JP2013/055042
§ 371 (c)(1),
(2) Date: Jul. 16, 2014

(87) PCT Pub. No.: WO2013/133094
PCT Pub. Date: Sep. 12, 2013

(65) Prior Publication Data
US 2014/0353553 A1 Dec. 4, 2014

(30) Foreign Application Priority Data

Mar. 7, 2012 (JP) ................................. 2012-050077

(51) Int. Cl.
| | | |
|---|---|---|
| C09B 23/00 | (2006.01) | |
| H01L 31/00 | (2006.01) | |
| H01L 51/00 | (2006.01) | |
| H01G 9/20 | (2006.01) | |
| C07D 333/24 | (2006.01) | |
| C07D 409/04 | (2006.01) | |
| C07D 409/12 | (2006.01) | |
| C07F 7/08 | (2006.01) | |
| C09B 23/01 | (2006.01) | |
| C09B 23/10 | (2006.01) | |
| C09B 57/00 | (2006.01) | |
| C07D 403/08 | (2006.01) | |
| H01L 31/0256 | (2006.01) | |

(52) U.S. Cl.
CPC .......... *H01G 9/2059* (2013.01); *C07D 333/24* (2013.01); *C07D 403/08* (2013.01); *C07D 409/04* (2013.01); *C07D 409/12* (2013.01); *C07F 7/0816* (2013.01); *C09B 23/005* (2013.01); *C09B 23/0058* (2013.01); *C09B 23/105* (2013.01); *C09B 57/008* (2013.01); *H01L 51/0068* (2013.01); *H01L 51/0072* (2013.01); *H01G 9/2031* (2013.01); *H01L 51/0064* (2013.01); *H01L 51/0074* (2013.01); *H01L 51/0094* (2013.01); *H01L 2031/0344* (2013.01); *Y02E 10/542* (2013.01)

(58) Field of Classification Search
CPC ...... H01G 9/20; H01G 9/2059; H01L 31/00; H01L 51/0052; H01L 2031/0344; C09B 23/00
See application file for complete search history.

(56) References Cited

U.S. PATENT DOCUMENTS 3,560,491 A 2/1971 Neeff

FOREIGN PATENT DOCUMENTS

| GB | 1119429 | 7/1968 |
| GB | 1141630 | 1/1969 |
| JP | 2000-299139 | 10/2000 |
| JP | 2011-122088 | 6/2011 |

OTHER PUBLICATIONS

Alternation of Charge Injection and Recombination in Dye-Sensitized Solar Cells by the Addition of Nonconjugated Bridge to Organic Dyes, Zhang et al., J. Phys. Chem. C 2013, 117, 2024-2031.*

(Continued)

*Primary Examiner* — Khanh Tuan Nguyen
*Assistant Examiner* — Haidung Nguyen
(74) *Attorney, Agent, or Firm* — Young & Thompson

(57) ABSTRACT

A novel compound represented by general formula (1), a carrier system including a carrier having the novel compound fixed thereon, and a photoelectric conversion device having the carrier system.

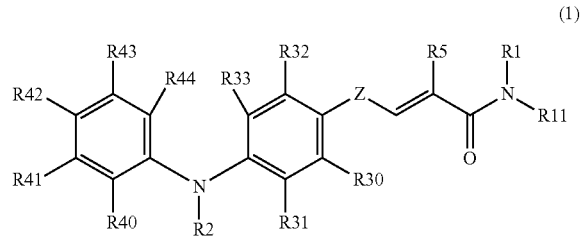

(1)

In formula (1), Z is a C1-C50 conjugated group; R1 is a C6-C20 aromatic hydrocarbon group, a C7-C20 aromatic hydrocarbon group substituted by an aliphatic hydrocarbon group, or a C1-C20 aliphatic hydrocarbon group, each substituted by carboxyl, cyano, amino, amide, or nitro, the aliphatic hydrocarbon group being optionally interrupted by —O—, etc.; R2 is hydrogen or an optionally substituted C1-C20 hydrocarbon group; R30, R31, R32, R33, R40, R41, R42, R43, and R44 are each hydrogen or optionally substituted hydrocarbon group, and adjacent two of them may be connected to form a ring; R5 is hydrogen or cyano; and R11 is represented by formula (11-1) or (11-2),
wherein n, ring A, and the like are as defined in the description.

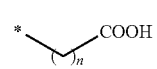

(11-1)

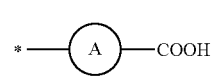

(11-2)

20 Claims, 1 Drawing Sheet

(56) References Cited

OTHER PUBLICATIONS

International Search Report PCT/JP2013/055042 dated May 14, 2013.
Written Opinion of ISA PCT/JP2013/055042 dated May 14, 2013.
Extended European search report, dated Oct. 16, 2015; Application No. 13758609.5.
Garcia-Iglesias et al., "Effect of anchoring groups in zinc phthalocyanine on the dye-sensitized solar cell performance and stability," Chemical Science, vol. 2, No. 6, Mar. 30, 2011, pp. 1145-1150.

* cited by examiner

COMPOUND AND CARRIER SYSTEM HAVING THE COMPOUND

TECHNICAL FIELD

This invention relates to a novel compound, a carrier system having the novel compound, and a photoelectric conversion device having the carrier system.

BACKGROUND ART

Dyes are widely used in a variety of technical fields. In the field of photoelectric conversion devices such as solar cells, for instance, dyes having photosensitizing properties have been used in dye-sensitized photoelectric conversion devices. Dye-sensitized photoelectric conversion devices are expected to theoretically achieve high efficiency and be produced at lower cost than those having a conventional silicone semiconductor.

A dye-sensitized photoelectric conversion device has an electrode having an oxide semiconductor using a dye carrier. In the dye-sensitized photoelectric conversion device, the dye is excited on absorbing light falling on the device and injects electrons into the carrier to perform photoelectric conversion.

Studies have been conducted on improvement on a carrier and the adsorbability of a dye (property of being adsorbed) onto a carrier as an approach to improve the conversion efficiency and durability of dye sensitized photoelectric conversion devices. That is, improvements on physical and chemical adsorbability of a dye would allow for efficient movement of the excited dye energy to the carrier and prevent the dye from desorving into the device, specifically into the electrolyte, and the like. Disclosed techniques for improving dye adsorbability include a dye molecule having a carboxyl group bonded thereto via an amide linkage (see patent document 1 below) and a dye molecule having two carboxyl groups (see patent document 2 below).

A solar cell, one of the main applications of the dye-sensitized photoelectric conversion device, is required to have high durability by the very nature of use. In this regard, a known dye and a photoelectric conversion device using the known dye have not yet achieved sufficient characteristics.

CITATION LIST

Patent Literature

Patent Literature 1: JP 2011-122088A
Patent Literature 2: JP 2000-299139A

SUMMARY OF THE INVENTION

Technical Problem

An object of the invention is to provide a novel compound, particularly a novel compound functioning as a dye exhibiting high adsorbability on a carrier, a carrier having the novel compound thereon, and a photoelectric conversion device having high efficiency and high durability.

Solution to Problem

As a result of extensive studies, the present inventors have discovered a novel compound having a specific structure and found that this compound accomplishes the above object. The present invention has been completed based on these findings.

The invention provides a novel compound represented by general formula (1) shown below, a carrier having the compound fixed thereon (hereinafter referred to as a carrier system), and a photoelectric conversion device comprising an electrode having the carrier system.

[Chemical Formula 1]

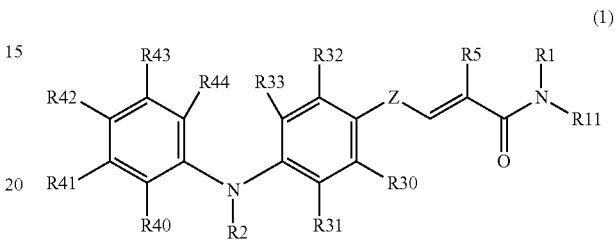

(1)

wherein Z represents a conjugated group having 1 to 50 carbon atoms selected from an unsaturated aliphatic hydrocarbon group, an aromatic hydrocarbon group, an aromatic heterocyclic group, and a group composed of one or more of these groups:

R1 represents an aromatic hydrocarbon group having 6 to 20 carbon atoms, an aromatic hydrocarbon group having 7 to 20 carbon atoms and substituted by an aliphatic hydrocarbon group, or an aliphatic hydrocarbon group having 1 to 20 carbon atoms, the aromatic hydrocarbon group having 6 to 20 carbon atoms, the substituted aromatic hydrocarbon group having 7 to 20 carbon atoms, and the aliphatic hydrocarbon group being substituted by at least one of a carboxyl group, a cyano group, an amino group, an amide group, and a nitro group, the aliphatic hydrocarbon group being optionally interrupted by an interrupting group selected from —O—, —COO—, —OCO—, —NR$^{24}$—, —NR$^{24}$COO—, and —OCONR$^{24}$— at up to 3 positions and, upon the interruption occurring at 2 or 3 positions, the interrupting groups not being adjacent to each other; wherein R$^{24}$ represents an aromatic hydrocarbon group having 6 to 10 carbon atoms, an aromatic hydrocarbon group having 7 to 15 carbon atoms and substituted by an aliphatic hydrocarbon group, or an aliphatic hydrocarbon group having 1 to 10 carbon atoms, the aromatic hydrocarbon group having 6 to 10 carbon atoms, the substituted aromatic hydrocarbon group having 7 to 15 carbon atoms, and the aliphatic hydrocarbon group being optionally substituted with a carboxyl group, a cyano group, an amino group, an amide group, or a nitro group;

R2 represents a hydrogen atom or an optionally substituted hydrocarbon group having 1 to 20 carbon atoms;

R30, R31, R32, R33, R40, R41, R42, R43, and R44 each independently represent a hydrogen atom or an optionally substituted hydrocarbon group; R30 and R31, R40 and R41, R41 and R42, R42 and R43, or R33 and R44 being optionally connected to each other to form a ring;

R5 represents a hydrogen atom or a cyano group; and

R11 represents a group represented by structural formula (11-1) or (11-2):

[Chemical Formula 1A]

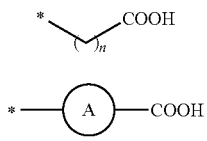

(11-1)

\*—(A)—COOH (11-2)

wherein n represents an integer of 1 to 4; ring A represents a benzene ring, a naphthalene ring, a cyclohexane ring, a cyclohexene ring, or a cyclohexadiene ring; the hydrogen atoms other than that of the carboxyl group in formulae (11-1) and (11-2) being optionally displaced by a carboxyl group, a cyano group, an amino group, an amide group, a nitro group, an aliphatic hydrocarbon group having 1 to 4 carbon atoms and substituted by at least one group selected from a carboxyl group, a cyano group, an amino group, an amide group and a nitro group, or an unsubstituted aliphatic hydrocarbon group having 1 to 4 carbon atoms.

Effect of the Invention

The novel compound of the invention has excellent adsorbability because of its carboxyl group and the group represented by R1, provides a highly efficient and highly durable carrier system and electrode, and is suited for use in photoelectric conversion devices such as solar cells.

DESCRIPTION OF EMBODIMENTS

Figure 1:
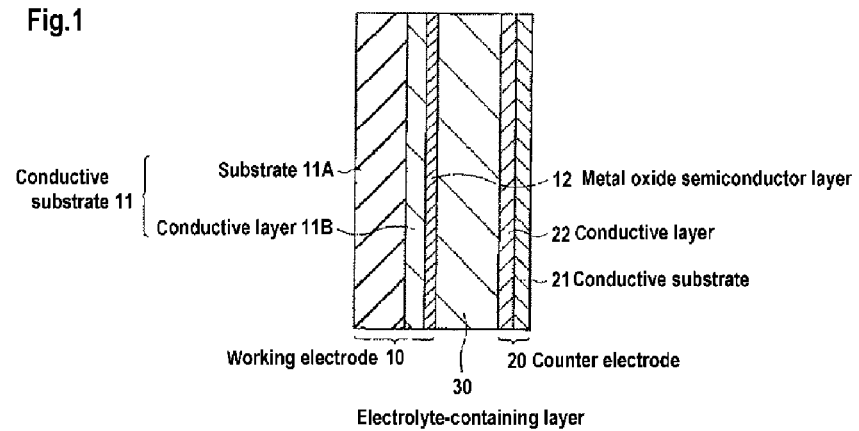
FIG. 1 schematically illustrates a cross-sectional structure of a photoelectric conversion device according to the invention.

The novel compound of the invention, the carrier system of the invention, and the photoelectric conversion device having the carrier system will be illustrated based on their preferred embodiments.

The novel compound of the invention will be described first.

The conjugated group as represented by Z in general formula (1) is not particularly limited as long as it is a pi-conjugated group and may have a substituent. As used herein, the term "pi-conjugated group" means a system in which unsaturated bonds are connected alternating with single bonds. Of the pi-conjugated groups as Z preferred are those in which the unsaturated bonds have a total of 4 to 60 carbon atoms, more preferably 4 to 40 carbon atoms.

Z preferably represents a group composed of 1 to 7 groups selected from the groups represented by formulae (Z-1) through (Z-10) shown below, more preferably a group containing at least one group represented by formula (Z-7), even more preferably a group composed solely of at least one group represented by formula (Z-7).

[Chemical Formula 2]

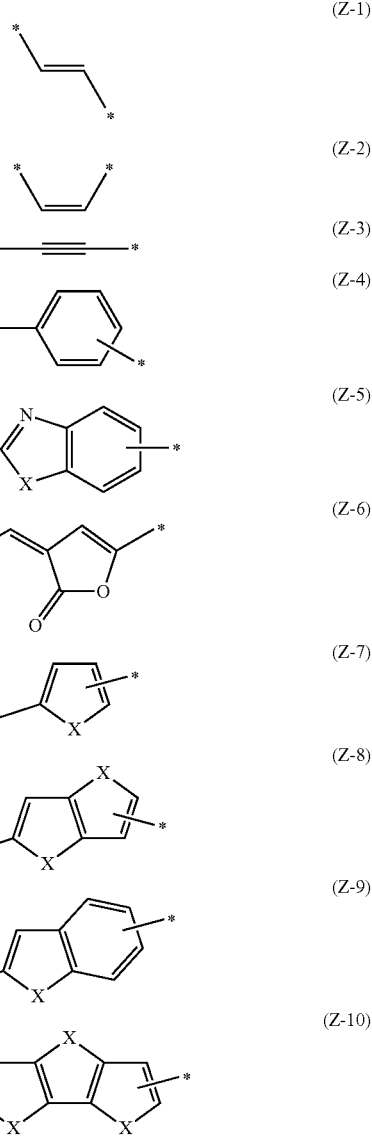

wherein X represents S, O, NR6, or SiR6R7; the hydrogen atoms other than that directly bonded to the nitrogen atom is optionally displaced by a fluorine atom, a chlorine atom, an iodine atom, a cyano group, a nitro group, —OR6, —SR6, —NR6R7, —SiR6R7R8, or an optionally substituted aliphatic hydrocarbon group: R6, R7, and R8 each represent a hydrogen atom or an optionally substituted hydrocarbon group.

Examples of the aliphatic hydrocarbon group which may substitute for the hydrogen atom in formulae (Z-1) through (Z-10) include alkyl groups, such as methyl, ethyl, propyl, isopropyl, cyclopropyl, butyl, sec-butyl, tert-butyl, isobutyl, amyl, isoamyl, tert-amyl, cyclopentyl, hexyl, 2-hexyl, 3-hexyl, cyclohexyl, bicyclohexyl, 1-methylcyclohexyl, heptyl, 2-heptyl, 3-heptyl, isoheptyl, tert-heptyl, n-octyl, isooctyl, tert-octyl, 2-ethylhexyl, nonyl, isononyl, and decyl; alkoxy groups, such as methoxy, ethoxy, propoxy, isopropoxy, butoxy, sec-butoxy, tert-butoxy, isobutoxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, nonyloxy, and decyloxy: alkylthio groups, such as methylthio, ethylthio, propylthio, isopropylthio, butylthio, sec-butylthio, tert-butylthio, isobutylthio, amylthio, isoamylthio, tert-amylthio, heylthio, cyclohexylthio, heptylthio, isoheptylthio, tert-heptylthio, n-octylthio, isooctylthio, tert-octylthio, and 2-ethylhexylthio; and alkenyl groups, such as vinyl, 1-methylethenyl, 2-methylethenyl, 2-propenyl, 1-methyl-3-propenyl, 3-butenyl, 1-methyl-3-butenyl, isobutenyl, 3-pentenyl, 4-hexenyl, cyclohexenyl, bicyclohexenyl, heptenyl, octenyl, decenyl, pentadecenyl, eicosenyl, and tricosenyl. These groups may be interrupted by —O—, —CO—, —COO—, —OCO—, —NHCO—, —NH—, NHCO— at 1 to 4 positions. The aliphatic hydrocarbon group may be substituted by fluorine, chlorine, iodine, cyano, nitro, hydroxyl, thiol, or amino.

Examples of the optionally substituted hydrocarbon group as represented by R6 or R7 include an aliphatic hydrocarbon group, an alicyclic hydrocarbon group, an aromatic hydrocarbon group, or a group composed of two or more of these hydrocarbon groups. Examples of the aliphatic hydrocarbon group include those described above as a substituent for the hydrogen atom of the groups of formulae (Z-1) to (Z-10). Examples of the alicyclic hydrocarbon group include cyclopropyl, cyclopentyl, cyclohexyl, and cycloheptyl. Examples of the aromatic hydrocarbon group include phenyl, naphthyl, benzyl, fluorenyl, and indenyl.

Examples of the substituent of the optionally substituted hydrocarbon groups represented by R6 and R7 include fluorine, chlorine, iodine, cyano, nitro, hydroxyl, thiol, and amino.

R1 in general formula (1) will be described.

Examples of the C6-C20 aromatic hydrocarbon group include phenyl, naphthyl, cyclohexylphenyl, biphenyl, terphenyl, fluorenyl, thiophenylphenyl, furanylphenyl, 2'-phenyl-propylphenyl, benzyl, and naphthylmethyl. These groups are substituted by at least one of carboxyl, cyano, amino, amide, and nitro groups. Examples of such substituted aromatic hydrocarbon groups include 2-carboxyphenyl, 3-carboxylphenyl, 4-carboxylphenyl, 2-cyanophenyl, 3-cyanophenyl, 4-cyanophenyl, 2-aminophenyl, 3-aminophenyl, 4-aminophenyl, phenylamido-4'-yl, 2-nitroamide, 3-nitroamide, 4-nitroamide, 3-carboxynaphthalene, 4-carboxynaphthalene, 5-carboxynaphthalene, 6-carboxynaphthalene, 6-carboxylnaphthalen-2-yl, 3-cyanonaphthalene, 4-cyanonaphthalene, 5-cyanonaphthalene, 4-carboxylphenylmethyl, and 4-cyanophenylmethyl.

Examples of the C1-C20 aliphatic hydrocarbon group include those described above as a substituent for the hydrogen atom of the groups of formulae (Z-1) to (Z-10). These groups are substituted by at least one of carboxyl, cyano, amino, amide, and nitro groups. Examples of such substituted groups include cyanomethyl, 2-cyanopethyl, 2-cyanopropyl, 3-cyanopropyl, carboxymethyl, 2-carboxyethyl, 2-carboxypropyl, 3-carboxymethyl, 2-carboxyethyl, 2-carboxypropyl, 3-carboxypropyl, methylamido, ethylamido, nitromethyl, 2-nitroethyl, and 3-nitropropyl.

Examples of the C7-C20 aromatic hydrocarbon group substituted by an aliphatic hydrocarbon group include the above described aromatic hydrocarbon groups substituted by the above described aliphatic hydrocarbon group(s). These groups are further substituted by at least one of carboxyl, cyano, amino, amido, and nitro groups. Examples of such substituted aromatic hydrocarbon groups include 2-carboxy-5-methylphenyl, 5-carboxy-2-methylphenyl, 4-carboxy-2,5-dimethylphenyl, and 4-cyano-2,5-dimethylphenyl.

The number of the substituents selected from carboxyl, cyano, amino, amido, and nitro groups that are essentially present in R1 is one to three, preferably one or two, more preferably one. Of these substituents preferred are carboxyl and cyano, with carboxyl being more preferred.

Examples of the optionally substituted C1-C20 hydrocarbon group as represented by R2 in general formula (1) include those having 1 to 20 carbon atoms out of the above-described optionally substituted hydrocarbon groups represented by R6. Examples of the optionally substituted hydrocarbon groups as represented by R30, R31, R32, R33, R40, R41, R42, R43, and R44 are the same as those described as examples of the optionally substituted hydrocarbon groups represented by R6.

R30 and R31, R40 and R41, R41 and R42, R42 and R43, or R33 and R44 may optionally be connected to each other to form a ring, such as a benzene ring or a dioxene ring.

Of the compounds of general formula (1) preferred are those in which R5 is cyano, or R11 is the group represented by structural formula (11-1) wherein n is 1 or 2. More preferred are those in which R5 is cyano, and R11 is the group of structural formula (11-1) wherein n is 1 or 2.

Of the compounds of general formula (1) also preferred are those represented by general formula (2):

[Chemical Formula 3]

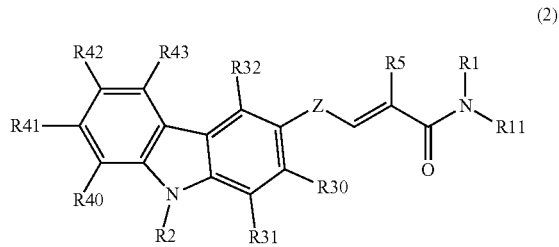

(2)

wherein Z, R1, R11, R2, R30, R31, R32, R40, R41, R42, R43, and R5 are as defined above.

Specific examples of the novel compound represented by general formula (1) include, but are not limited to, compound Nos. 1 through 42 shown below. In the formulae below, Hex represents hexyl.

[Chemical Formula 4-1]
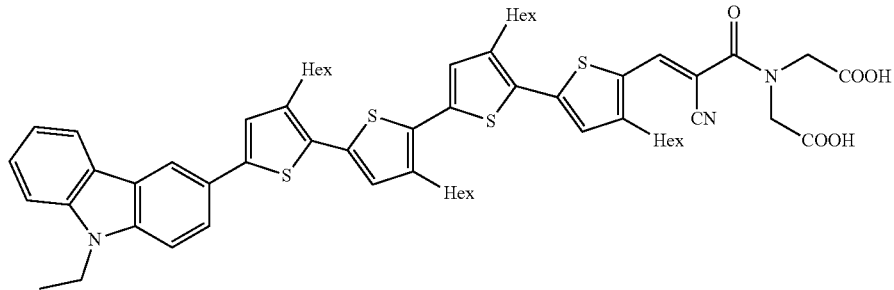
No. 1
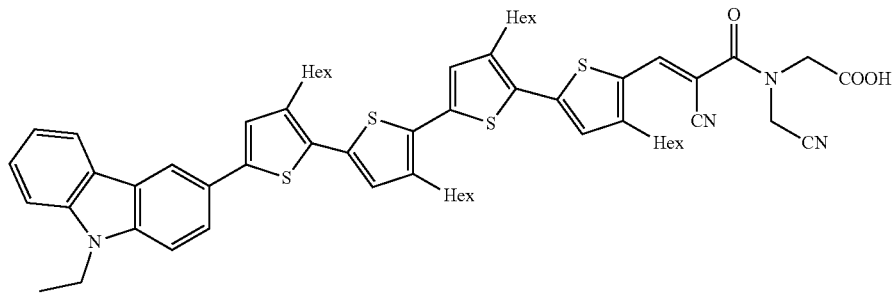
No. 2
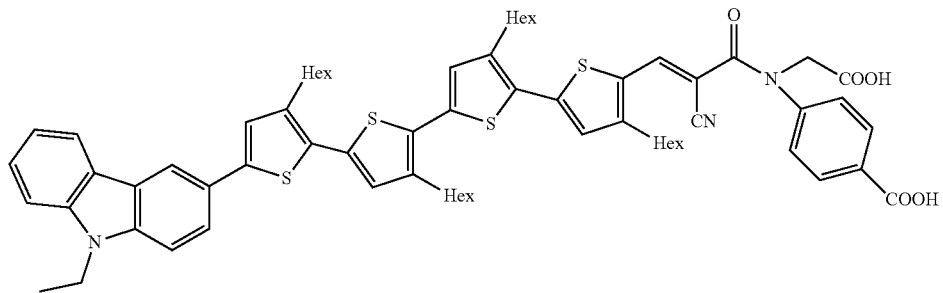
No. 3
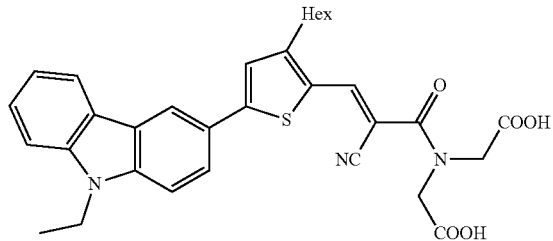
No. 4
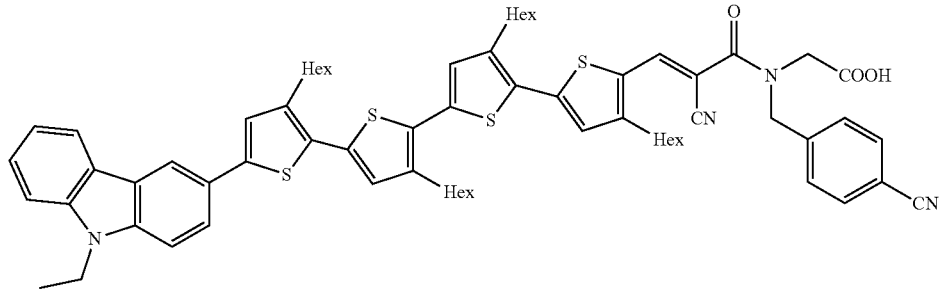
No. 5

No. 6
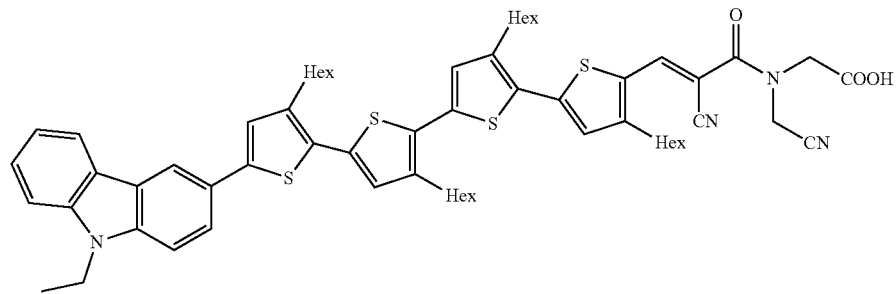
No. 7
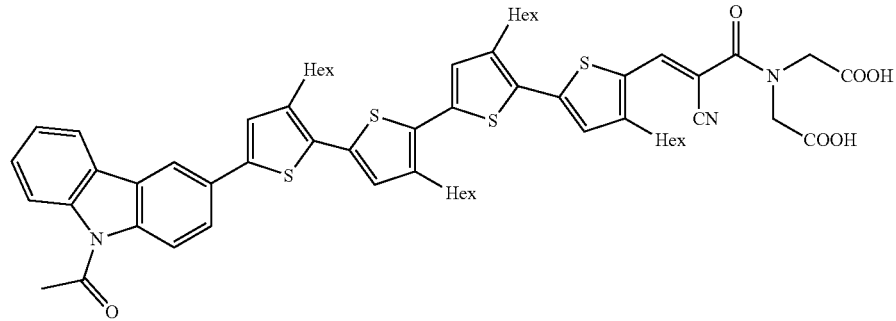
No. 8
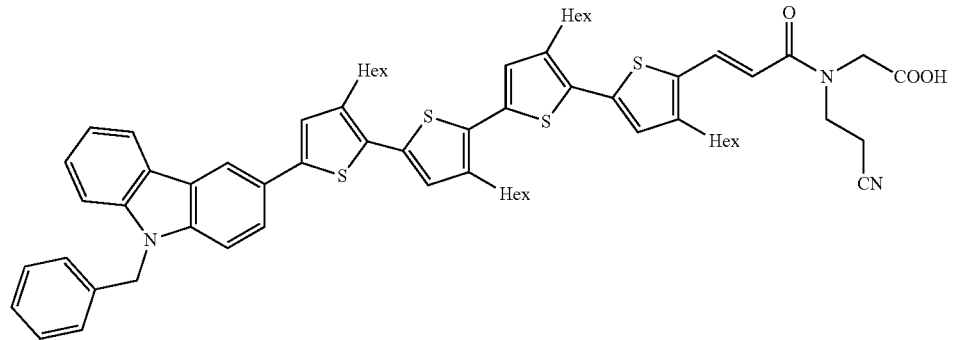
No. 9
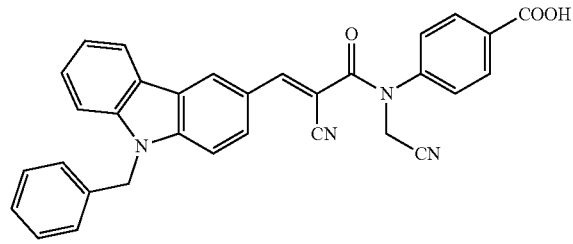
No. 10
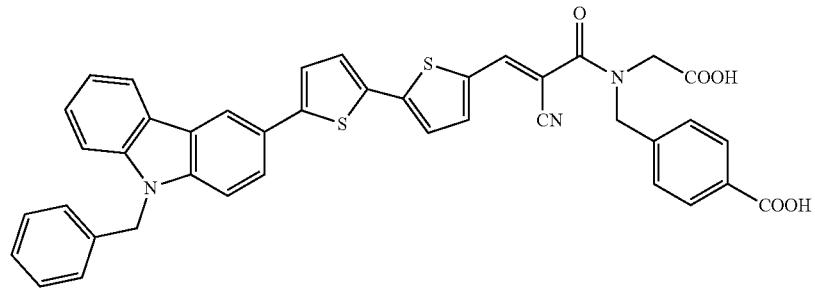

-continued
No. 11
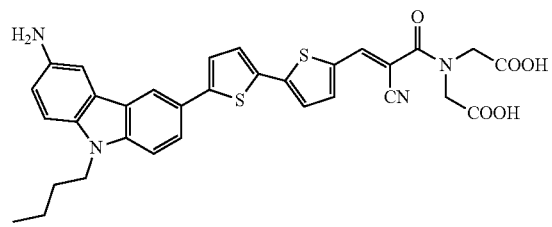
No. 12
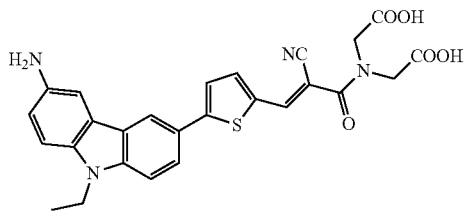
No. 13
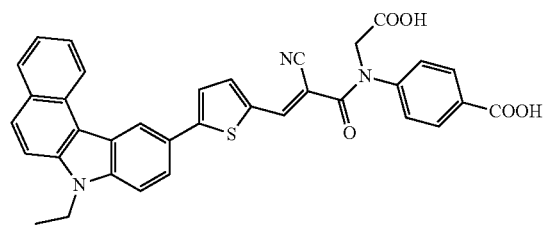
No. 14
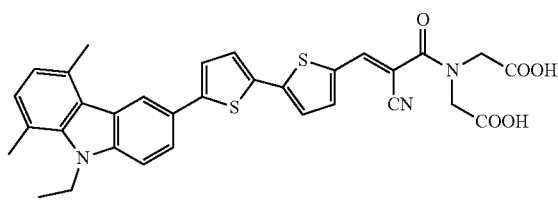
[Chemical Formula 4-2]
No. 15
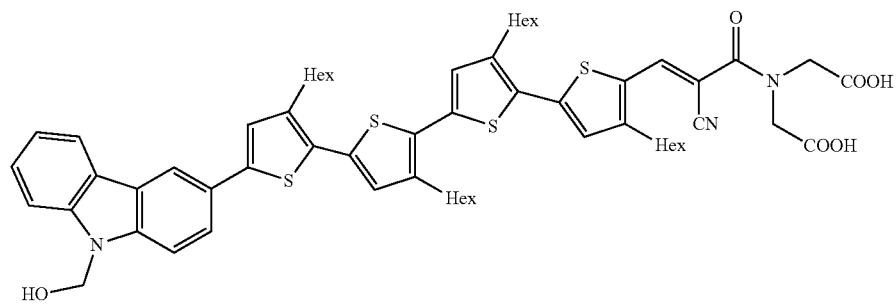
No. 16
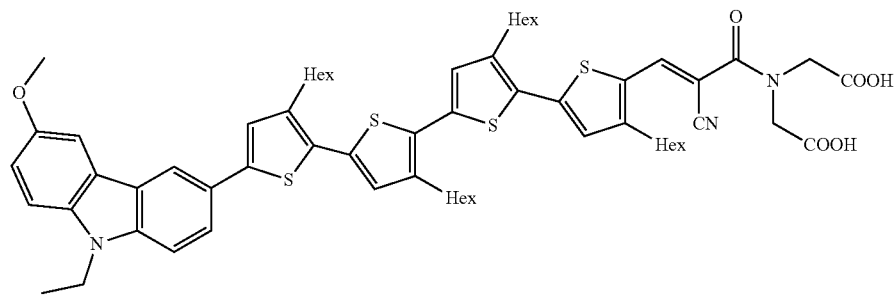
No. 18
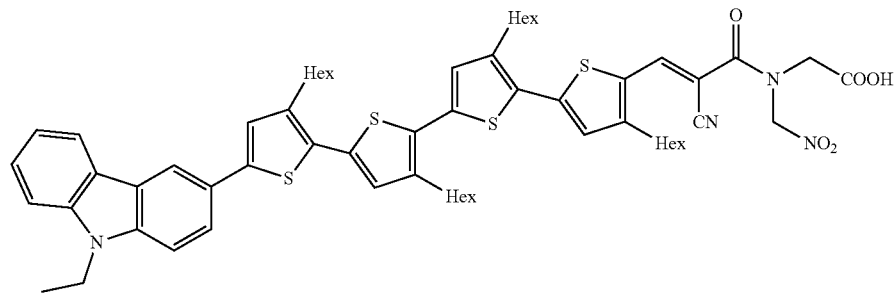

-continued
No. 19
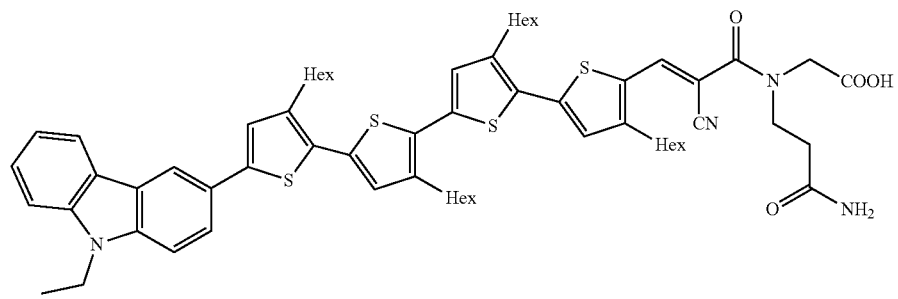
No. 20
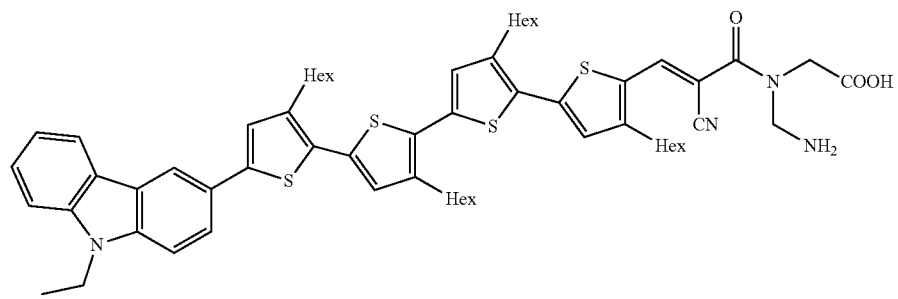
No. 21
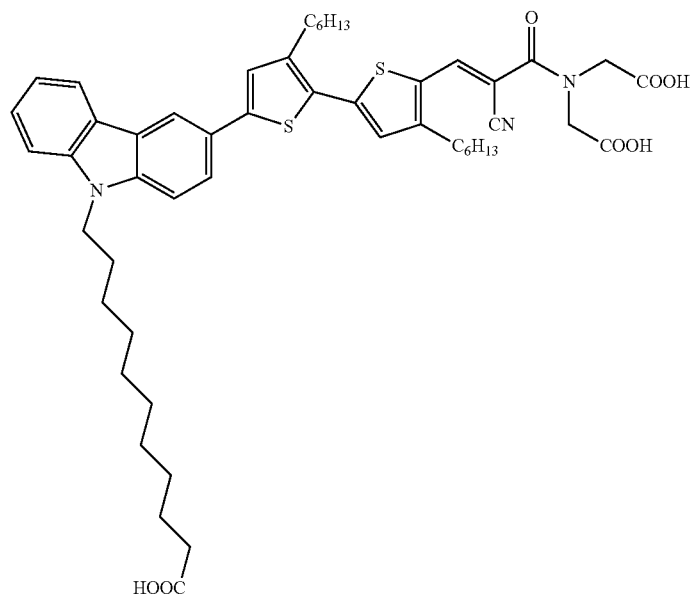
No. 22
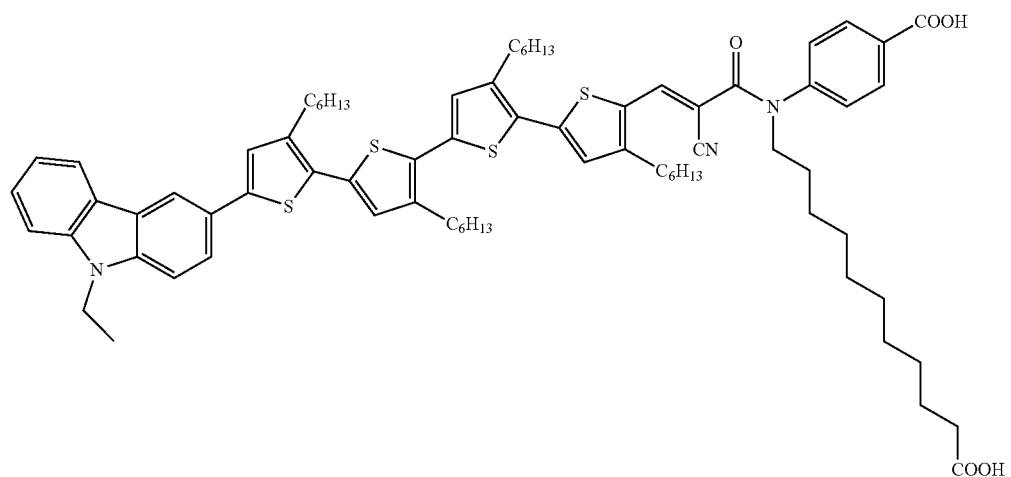

No. 23
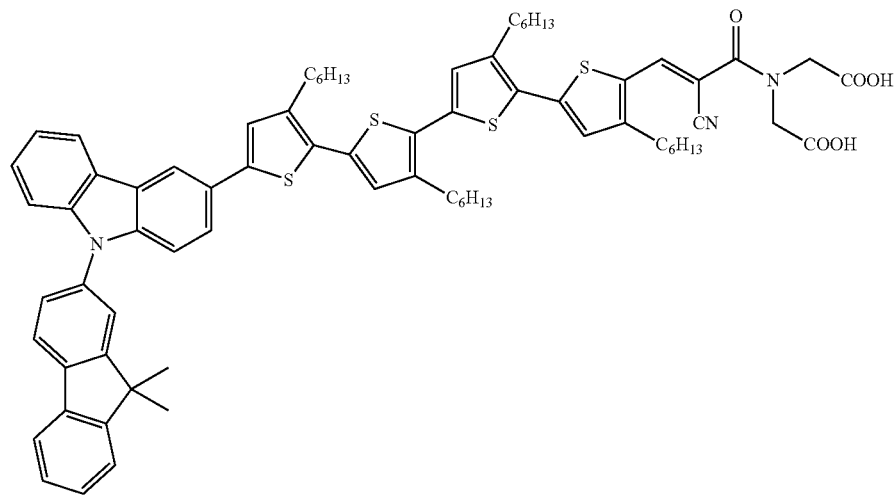
No. 24
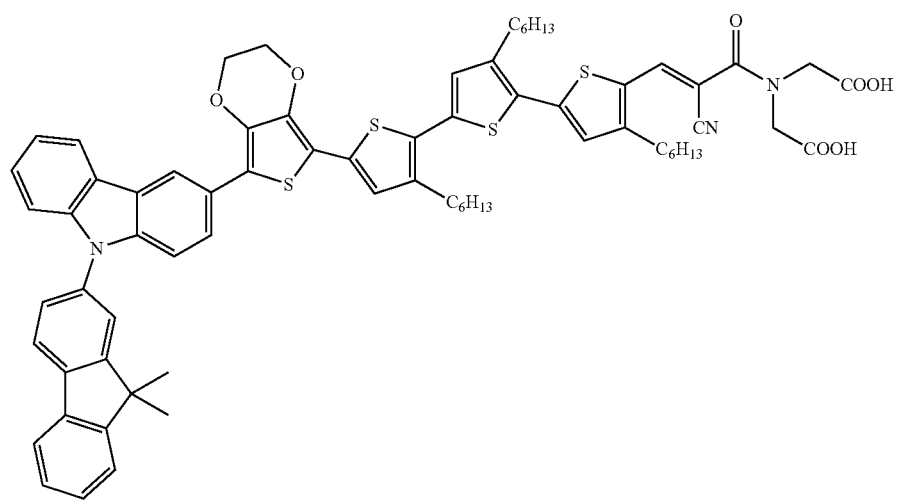
[Chemical Formula 4-3]
No. 25
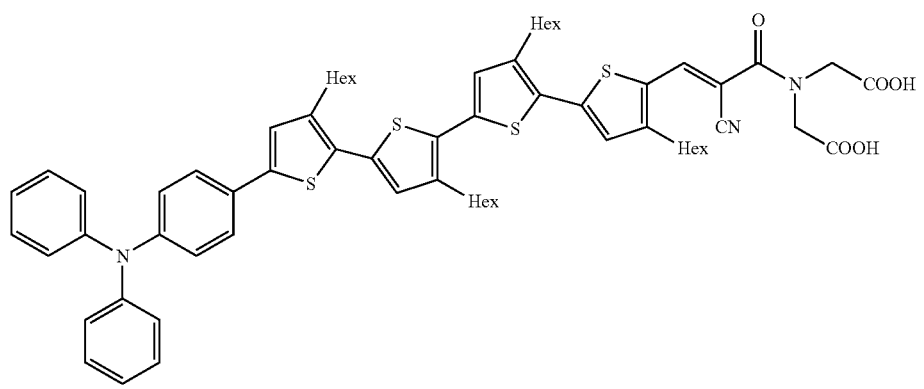

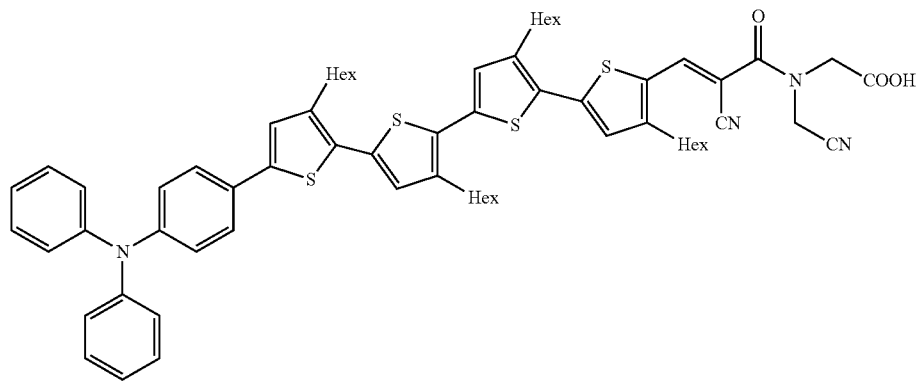
No. 26
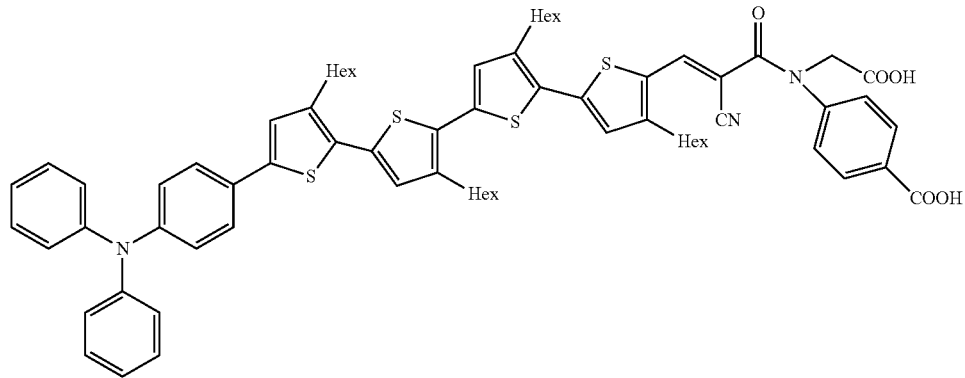
No. 27
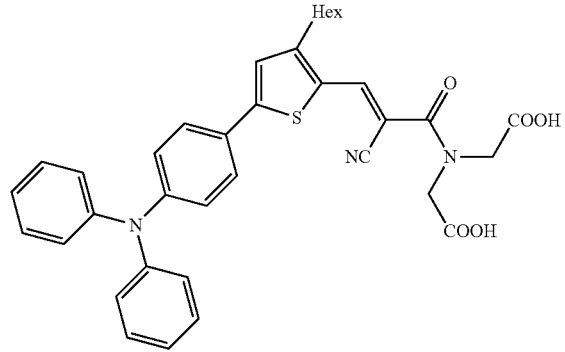
No. 28
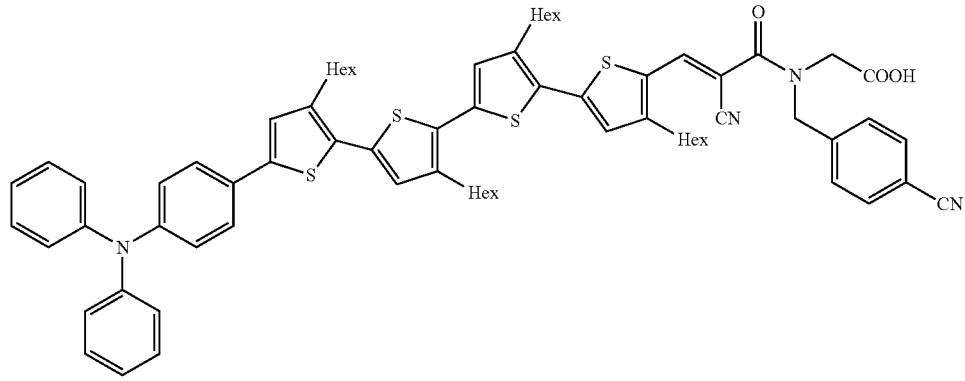
No. 29

-continued
No. 30
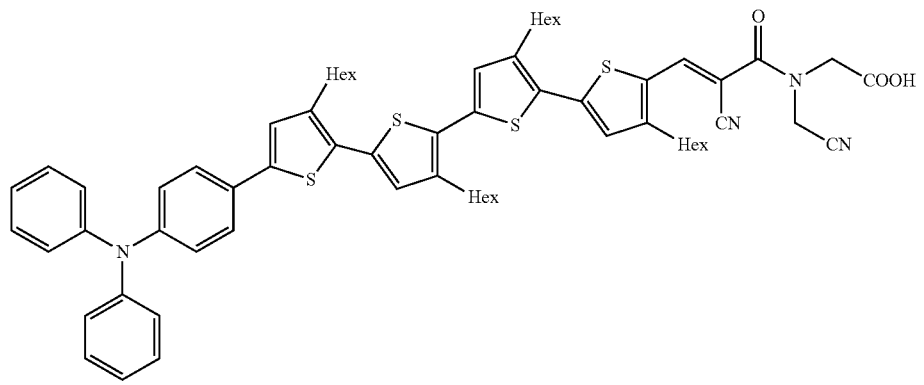
No. 31
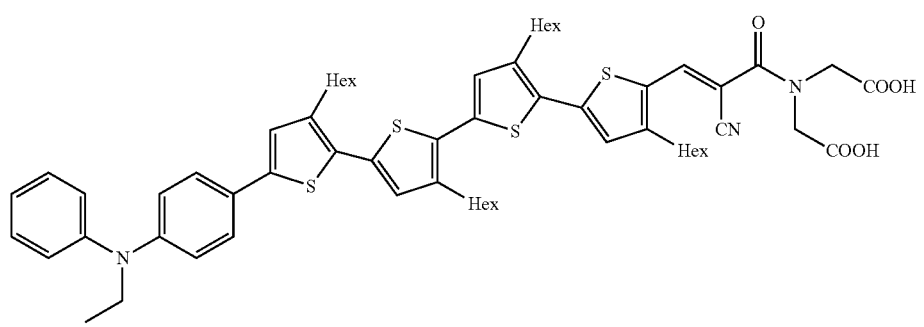
No. 32
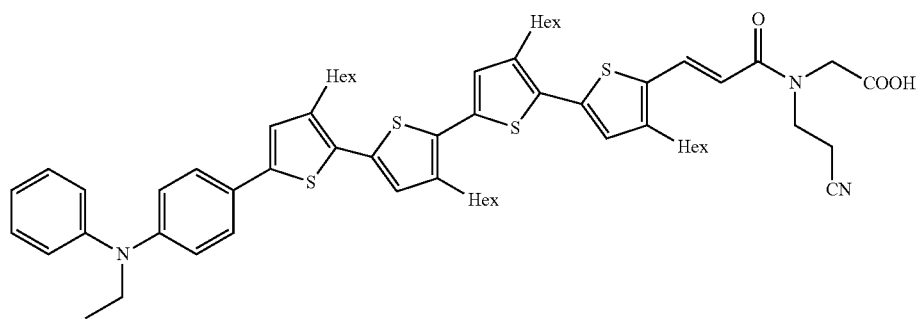
[Chemical Formula 4-4]
No. 33
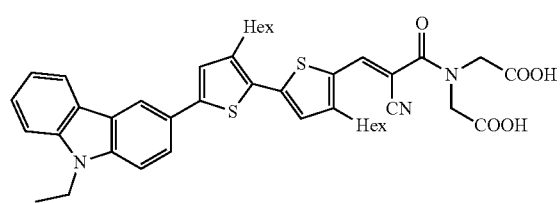
No. 34
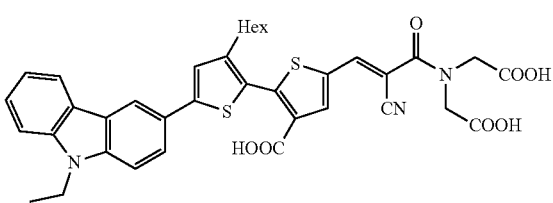
No. 35
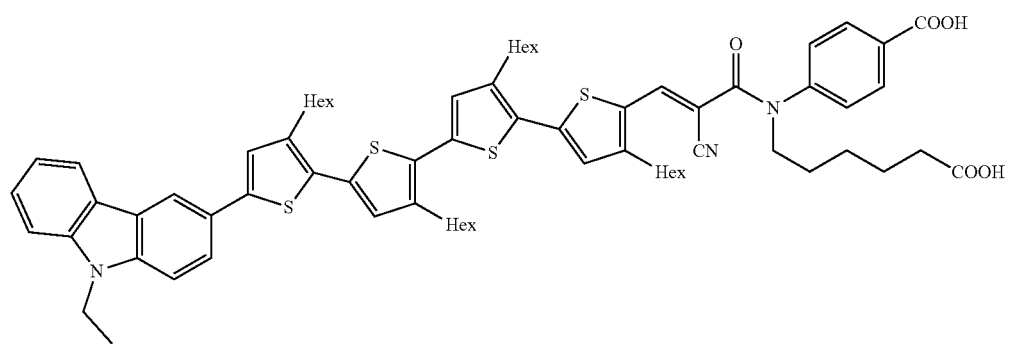

-continued
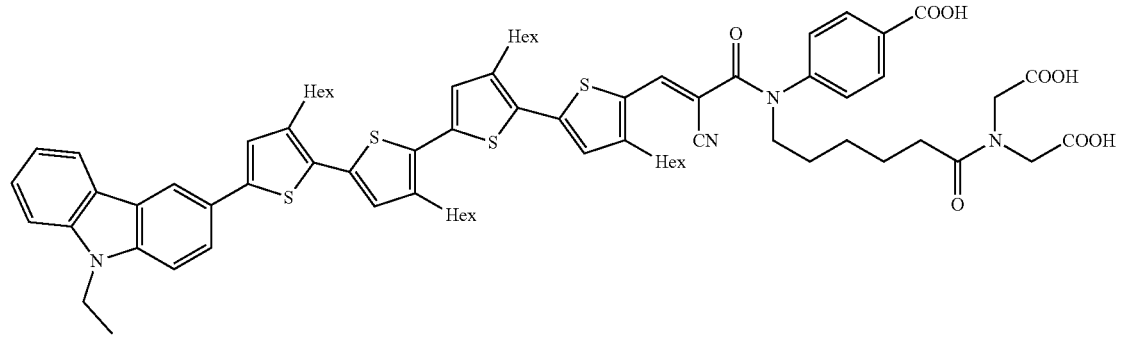
No. 36
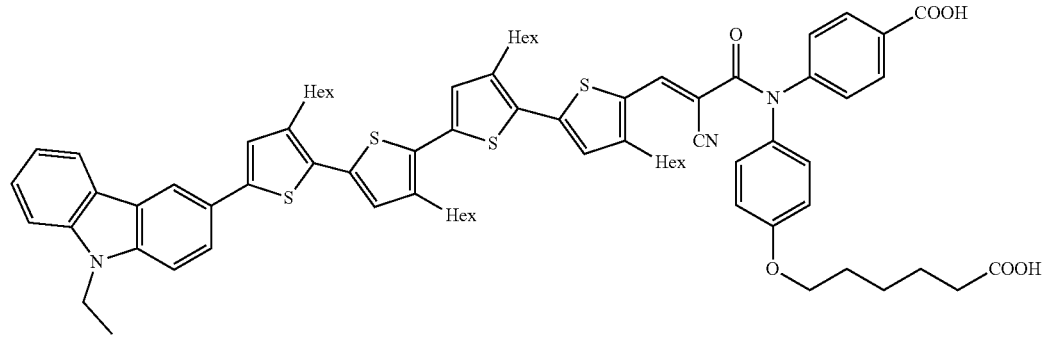
No. 37
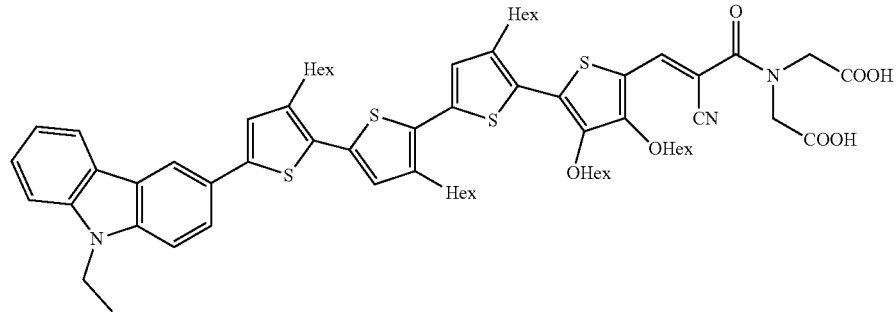
No. 38
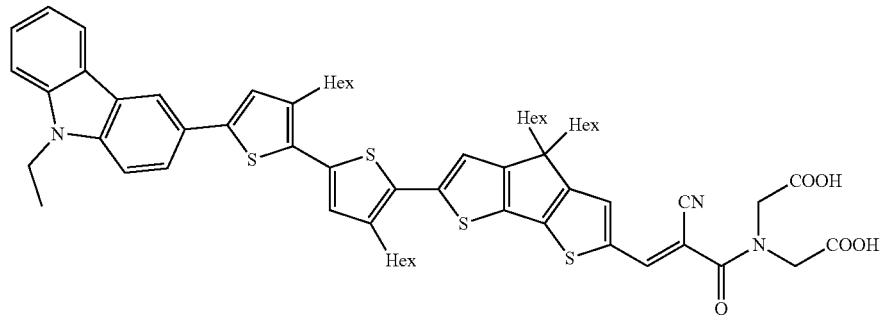
No. 39
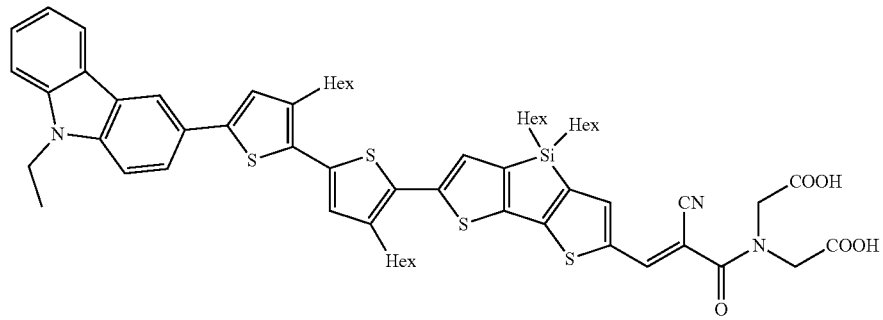
No. 40

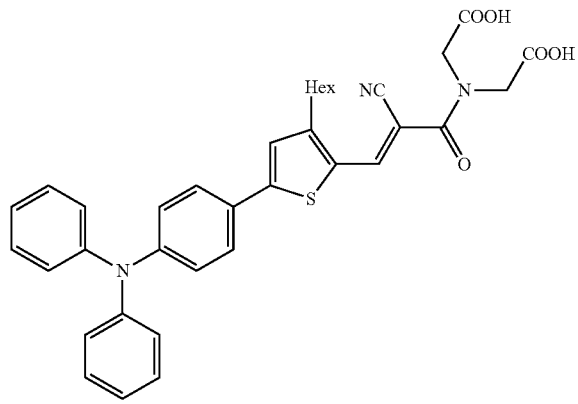

No. 41

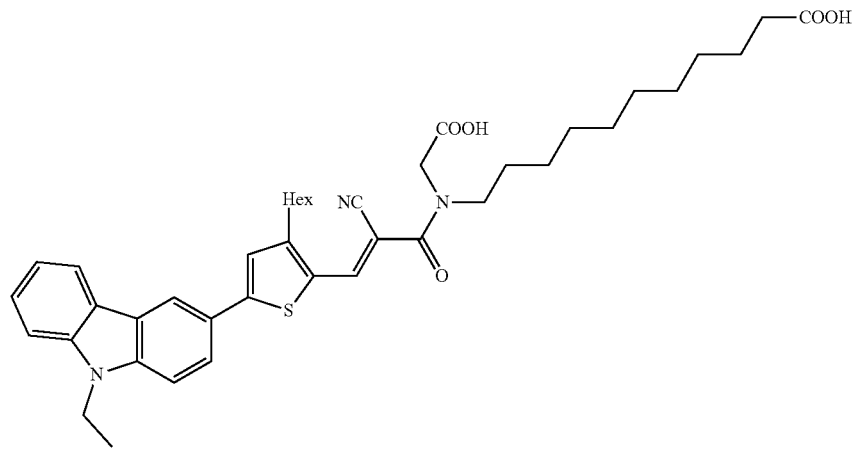

No. 42

The compound of general formula (1) is obtained using publicly disclosed or commonly known reactions. The process for synthesizing the compound of formula (1) is not particularly limited. A typical example of the process for the synthesis includes converting a conjugated carboxylic acid (10) having a carboxyl group to an acid chloride (11), causing a secondary amine compound (12) having a protected carboxyl group to react on the acid chloride (11) to synthesize an amide compound (13), and deprotecting the carboxyl group using trifluoroacetic acid. In the reaction scheme shown below, a compound of general formula (1) in which R11 is represented by structural formula (11-1), designated general formula (1'), is synthesized. The reagents used in the reactions may be changed where necessary.

[Chemical Formula 5]

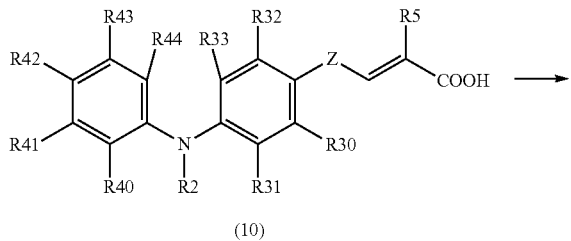

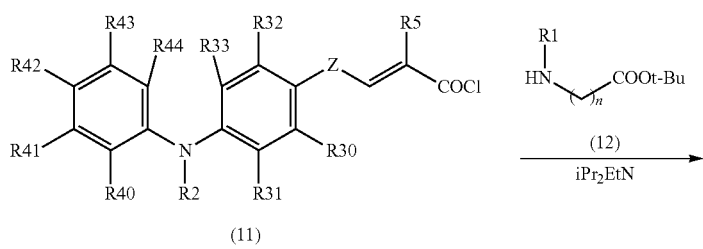

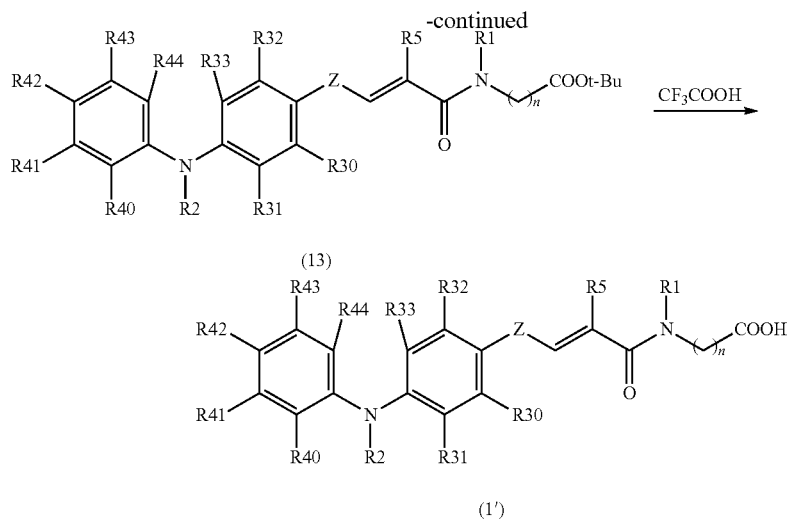

(1')

wherein Z, R1, R2, R30, R31, R32, R33, R40, R41, R42, R43, R44, R5, and n are as defined above.

The novel compound of the invention is suitably used as fixed on a carrier for application to photoelectric conversion devices. The novel compound of the invention also finds applications as intermediates for optical recording materials, pharmaceuticals, agricultural chemicals, aroma chemicals, and dyes; various functional materials, starting materials for various polymers; photoelectrochemical cells, nonlinear optical devices, electrochromic displays, holographic devices, organic semiconductors, organic ELs; silver halide photographic materials, photosensitizers; colorants in printing inks, inkjet inks, electrophotographic color toners, cosmetics, and plastics; stains for proteins, luminescent dyes for detection; material for making artificial quartz, paints, synthetic catalysts, catalyst carriers, surface coating thin film materials, silicone rubber crosslinking agents, binders; and so on.

The carrier system according to the invention will then be described.

Examples of materials used as a carrier in the invention include organic resins, such as acrylic resins and fluororesins; metal oxides, such as titanium oxide, zinc oxide, and aluminum oxide; silicon oxide, zeolite, and activated carbon. Preferred are those having a porous surface. The carrier system of the invention is characterized in that the compound to be fixed onto the carrier is the compound represented by general formula (1). The compound may be fixed to the carrier by known methods including gas or liquid phase adsorption. For example, liquid phase adsorption may be carried out by dissolving the compound of the invention in a solvent and immersing the carrier in the solution.

The form of the carrier is not particularly limited and may be chosen from, for example, thin film, powder, and granules as appropriate to the use. The size of the carrier and the amount of the compound of the invention to be fixed thereto are not particularly limited and may be chosen as appropriate to the use.

The carrier system having the novel compound of the invention is suited for use in a photoelectric conversion device hereinafter described. It is also useful in catalysts, toners, and so forth.

The photoelectric conversion device according to the invention will then be described.

The photoelectric conversion device of the invention is a dye-sensitized photoelectric conversion device having the same structure as conventional dye-sensitized photoelectric conversion devices, except that the novel compound of the invention is used as a dye. A typical example of the configuration of the photoelectric conversion device of the invention will be described with reference to FIGS. 1 and 2.

Figure 2:
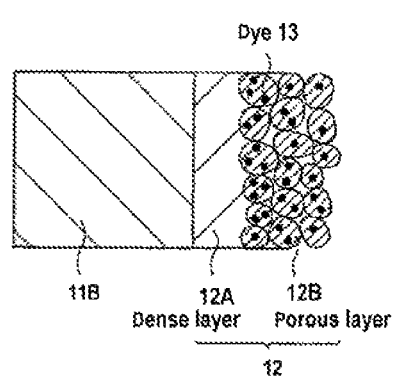
FIG. 2 is an enlarged view of an essential part of the photoelectric conversion device of the invention shown in FIG. 1.

FIG. 1 schematically shows a cross-sectional structure of a photoelectric conversion device according to the invention, and FIG. 2 is an enlarged view of an essential part of the photoelectric conversion device of the invention shown in FIG. 1. The photoelectric conversion device of FIGS. 1 and 2 is a principal part of a dye-sensitized solar cell. The photoelectric conversion device includes a working electrode 10 and a counter electrode 20 facing each other. At least one of the working electrode 10 and the counter electrode 20 is light-transmissive.

The working electrode 10 has, for example, an conductive substrate 11, a metal oxide semiconductor layer 12 provided on one side of the substrate 11 (on the side facing the counter electrode 20), and a dye 13 fixed to the metal oxide semiconductor layer 12. In the photoelectric conversion device of the invention the dye 13 is the novel compound represented by general formula (1) according to the invention. The carrier system according to the invention is a composite system composed of the novel compound of the invention as a dye and the metal oxide semiconductor layer 12 as a carrier.

The working electrode functions as a negative electrode of an outer circuit. The conductive substrate 11 is, for example, composed of an insulating substrate 11A and an conductive layer 11B on the surface of the insulating substrate 11A.

Suitable materials of the substrate 11A include insulating materials, such as glass and plastics. Plastics are used in the form of transparent polymer film. The plastics include tetraacetyl cellulose (TAC), polyethylene terephthalate (PET), polyethylene naphthalate (PEN), syndiotactic polystyrene (SPS), polyphenylene sulfide (PPS), polycarbonate (PC), polyarylate (PAR), polysulfone (PSF), polyester sulfone (PES), polyetherimide (PEI), cyclic polyolefins, and brominated phenoxy resins.

The conductive layer 11B is exemplified by a thin film of an electroconductive metal oxide, such as indium oxide, tin oxide, indium-tin complex oxide (ITO), or fluorine-doped tin oxide (FTO or F—SnO$_2$), a thin film or mesh of a metal, such as gold (Au), silver (Ag), or platinum (Pt), or an electroconductive polymer film.

The conductive substrate 11 may be a monolithic structure made of an electroconductive material. In this case, examples of the material of the conductive substrate 11 include electroconductive metal oxides, such as indium oxide, tin oxide, indium-tin complex oxide, or fluorine-doped tin oxide, metals, such as gold, silver, or platinum, and electroconductive polymers.

The metal oxide semiconductor layer 12 is a carrier having the dye 13 supported thereon. It has, for example, a porous structure as illustrated in FIG. 2. The metal oxide semiconductor layer 12 is formed of a dense layer 12A and a porous layer 12B. The dense layer 12A is formed on the interface between the conductive substrate 11 and is preferably dense and less-porous, more preferably filmy. The porous layer 12B is formed on the surface in contact with the electrolyte-containing layer 30. It preferably has a structure with many voids and a large surface area, more preferably a structure composed of porous particles adhering to one another. The metal oxide semiconductor layer 12 may have a single layer structure of film form. In the invention, the carrier system is a system in which the dye 13 is bonded or adsorbed to the porous layer 12B chemically, physically, or electrically.

Examples of the material (metal oxide semiconductor material) contained in the metal oxide semiconductor layer 12 include titanium oxide, zinc oxide, tin oxide, niobium oxide, indium oxide, zirconium oxide, tantalum oxide, vanadium oxide, yttrium oxide, aluminum oxide, and magnesium oxide. Inter alia, titanium oxide and zinc oxide are preferred; for they provide high conversion efficiency. These metal oxide semiconductor materials may be used either individually or in combination of two or more thereof in the form, e.g., of mixture, mixed crystal, solid solution, or one on surface of another. For example, titanium oxide and zinc oxide may be used in combination.

The metal oxide semiconductor layer 12 having a porous structure can be formed by, for example, electrodeposition, coating, or firing. Electrodeposition to form the metal oxide semiconductor layer 12 is carried out by immersing the conductive substrate 11 in an electrolytic bath containing a particulate metal oxide semiconductor material to cause the particles to adhere to and precipitate on the conductive layer 11B of the conductive substrate 11. In the case of the coating method, a dispersion of a particulate metal oxide semiconductor material (metal oxide slurry) is applied to the conductive substrate 11 and then dried to remove the dispersing medium. In the case of the firing method, the metal oxide slurry is applied to the conductive substrate 11 and dried in the same manner as in the coating method, followed by firing. The electrodeposition or coating method is advantageous in that a less heat-resistant plastic material or polymer film material is allowed to be used to form the substrate 11A thereby making it possible to provide a highly flexible electrode.

The metal oxide semiconductor layer 12 may be treated with an organic base, a urea derivative, or a cyclic saccharide chain. Examples of the organic base include diarylamines, triarylamines, pyridine, 4-t-butylpyridine, polyvinylpyridine, quinoline, piperidine, and amidines. The treatment may be effected either before or after the hereinafter described adsorption of the dye 13. The treatment may be carried out by immersion. In using a solid treating agent, the treating agent is dissolved in an organic solvent to prepare a solution, in which the metal oxide semiconductor layer 12 is immersed.

The dye 13 is, for example, in a state adsorbed onto the metal oxide semiconductor layer 12. The dye 13 includes at least one dye (sensitizing dye) capable of being excited on absorbing incident light and injecting electrons to the metal oxide semiconductor layer 12. In the photoelectric conversion device of the invention, the novel compound of general formula (1) of the invention corresponds to the dye 13. When the novel compound of the invention is used as the dye 13, the dye 13 as a whole achieves an increased rate of electron injection into the metal oxide semiconductor layer 12 per unit quantity of incident light, thereby to improve the conversion efficiency.

It is only necessary for the dye 13 to contain at least one novel compound represented by general formula (1). That is, the dye 13 may contain other dyes, such as organic dyes (hereinafter referred to as other organic dye(s)) and organic metal complex compounds, preferably dyes having a group capable of being adsorbed onto the metal oxide semiconductor layer 12 (i.e., the carrier).

Examples of the other organic dyes include eosin Y, dibromofluorescein, fluorescein, rhodamine B, pyrrogallol, dichlorofluorescein, Erythrosine B (registered trade name), fluorescin, merbromin, cyanine dyes, merocyanine disazo dyes, trisazo dyes, anthraquinone dyes, polycyclic quinone dyes, indigo dyes, diphenylmethane dyes, trimethylmethane dyes, quinoline dyes, benzophenone dyes, naphthoquinone dyes, perylene dyes, fluorenone dyes, squarylium days, azulenium dyes, perinone dyes, quinacridone dyes, metal-free phthalocyanine dyes, metal-free porphyrine dyes, and metal-free azaporphyrin dyes.

Examples of the organic metal complex compounds include those having both an ionic coordinate bond formed between a nitrogen anion of an aromatic heterocyclic ring and a metal cation and a nonionic coordinate bond formed between a nitrogen atom or a chalcogen atom and a metal cation and those having both an ionic coordinate bond formed between an oxygen or sulfur anion and a metal cation and a nonionic coordinate bond formed between a nitrogen or chalcogen atom and a metal cation. Specific examples of the organic metal complex compounds include metallophthalocyanine dyes, such as copper phthalocyanine, titanyl phthalocyanine, cobalt phthalocyanine, nickel phthalocyanine, and iron phthalocyanine; metallonaphthalocyanine dyes, metalloporphyrin dyes, metalloazaporphyrin dyes; and bipyridyl, terpyridyl, phenanthroline, bicinchoninate, azo, or quinolinol metal complexes using ruthenium, iron, or osmium, and other ruthenium complexes.

The dye 13 may contain, in addition to the above described dye, one or more additives, such as dye association inhibitors exemplified by cholic acid compounds represented by chemical formula (14) below. These compounds may be used either individually or as a mixture of two or more thereof.

[Chemical Formula 6]

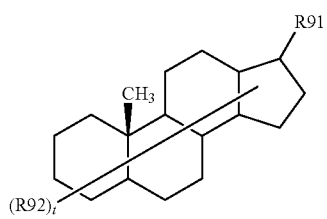

(14)

wherein R91 represents an alkyl group having an acidic group or an alkoxysilyl group; R92 represents a group bonded to any of carbon atoms constructing the steroid skeleton and selected from a hydroxyl group, a halogen atom, an alkyl group, an alkoxy group, an aryl group, a heterocyclic group, an acyl group, an acyloxy group, an oxycarbonyl group, an oxo group, an acidic group, an alkoxysilyl group, and derivatives of these groups; a plurality of R92 groups may be the same or different; t represents an integer of 1 to 5; and the carbon-to-carbon bonds constructing the steroid skeleton may be either a single bond or a double bond.

The counter electrode 20 is composed, e.g., of an conductive substrate 21 and an conductive layer 22 provided thereon and functions as a positive electrode of an outer circuit. Materials for making the conductive substrate 21 include those described for making the substrate 11A of the conductive substrate 11 of the working electrode 10. The conductive layer 22 comprises, for example, at least one electroconductive material and, if necessary, a binder. Examples of the electroconductive material for use in the conductive layer 22 include metals, such as platinum, gold, silver, copper (Cu), rhodium (Rh), ruthenium (Ru), aluminum (Al), magnesium (Mg), and indium (In), carbon (C), and electroconductive polymers. Examples of the binder for use in the conductive layer 22 include acrylic resins, polyester resins, phenol resins, epoxy resins, cellulose, melamine resins, fluoroclastomers, and polyimide resins. The counter electrode 20 may have a single layer structure formed of the conductive layer 22.

The electrolyte-containing layer 30 comprises, for example, a redox electrolyte containing an oxidation-reduction couple. Examples of the redox electrolyte include an $I^-/I_3^-$ couple, a $Br^-/Br_3^-$ couple, a quinone/hydroquinone couple, a cobalt complex, and a nitroxyl radical compound. Specifically, the redox electrolyte is exemplified by a halide/halogen couple, such as an iodide/iodine couple or a bromide/bromine couple. Examples of the halide include a cesium halide, a quaternary alkylammonium halide, an imidazolium halide, a thiazolium halide, an oxazolium halide, a quinolinium halide, and a pyridinium halide. Specifically, examples of the iodide include cesium iodide; quaternary alkylammonium iodides, such as tetraethylammonium iodide, tetrapropylammonium iodide, tetrabutylammonium iodide, tetrapentylammonium iodide, tetrahexylammonium iodide, tetraheptylammonium iodide, and trimethylphenylammonium iodide; imidazolium iodides, such as 3-methylimidazolium iodide and 1-propyl-2,3-dimethylimidazolium iodide; thiazolium iodides, such as 3-ethyl-2-methyl-2-thiazolium iodide, 3-ethyl-5-(2-hydroxyethyl)-4-methylthiazolium iodide, and 3-ethyl-2-methylbenzothiazolium iodide; oxazolium iodides, such as 3-ethyl-2-methylbenzoxazolium iodide; quinolinium iodides, such as 1-ethyl-2-methylquinolinium iodide; and pyridinium iodides. Examples of the bromides include quaternary alkylammonium bromides. Of the halide/halogen couples preferred are couples of at least one of the above listed iodides and iodine.

The redox electrolyte may be, for example, a combination of an ionic liquid and a halogen. In this case, the redox electrolyte may further contain the above described halide. Examples of the ionic liquid include those usable in electric batteries and solar cells, such as those disclosed in *Inorg. Chem.*, 1996, 35, pp. 1168-1178, *Electrochemistry*, 2002, 2, pp. 130-136, U.S. Pat. Nos. 5,728,487A, and 5,683,832A. Preferred of them are salts whose melting point is below room temperature (25° C.) or salts the melting point of which is higher than room temperature but which are liquefied at room temperature on dissolving with other fused salt. Specific examples of the ionic liquids are anions and cations described below.

Examples of cations of ionic liquids are ammonium, imidazolium, oxazolium, thiazolium, oxadiazolium, triazolium, pyrrolidinium, pyridinium, piperidinium, pyrazolium, pyrimidinium, pyridinium, triazinium, phosphonium, sulfonium, carbazolium, indolium, and derivatives thereof. They may be used either individually or as a mixture of two or more thereof. Specific examples include 1-methyl-3-propylimidaqzolium, 1-butyl-3-methylimidazolium, 1,2-dimethyl-3-propylimidazolium, and 1-ethyl-3-methylimidazolium.

Examples of anions of ionic liquids include metal chloride ions, e.g., $AlCl_4^-$ and $Al_2Cl_7^-$; fluorine-containing anions, such as $PF_6^-$, $BF_4^-$, $CF_3SO_3^-$, $N(CF_3SO_2)_2^-$, $F(HF)_n^-$, and $CF_3COO^-$; fluorine-free cations, such as $NO_3^-$, $CH_3COO^-$, $C_6H_{11}COO^-$, $CH_3OSO_3^-$, $CH_3OSO_2^-$, $CH_3SO_3^-$, $CH_3SO_2^-$, $(CH_3O)_2PO_2^-$, $N(CN)_2^-$, and $SCN^-$; and other halide ions, such as iodide ions and bromide ions. These anions may be used either individually or as a mixture of two or more thereof. Preferred of these anions of ionic liquids are iodide ions.

The electrolyte-containing layer 30 may be a liquid electrolyte (electrolyte solution) prepared by dissolving the redox electrolyte in a solvent or a solid polymer electrolyte in which an electrolyte solution is held in a polymer matrix. The electrolyte-containing layer 30 may also be a pseudo-solid (pasty) electrolyte containing a mixture of an electrolyte solution and a particulate carbon material, such as carbon black. The pseudo-solid electrolyte containing a carbon material does not need to contain a halogen simple substance because the carbon material functions to catalyze an oxidation-reduction reaction. The redox electrolyte may contain one or more organic solvents capable of dissolving the described halide or ionic liquid. The solvents include electrochemically inert solvents, such as acetonitrile, tetrahydrofuran, propionitrile, butyronitrile, methoxyacetonitrile, 3-methoxypropionitrile, valeronitrile, dimethyl carbonate, ethylmethyl carbonate, ethylene carbonate, propylene carbonate, N-methylpyrrolidone, pentyl alcohol, quinoline, N,N-dimethylformamide, γ-butyrolactone, dimethyl sulfoxide, and 1,4-dioxane.

For the purpose of improving power generation efficiency, durability, and the like of the photoelectric conversion device, the electrolyte-containing layer 30 may contain acyclic saccharides (see JP 2005-093313A), pyridine compounds (see JP 2003-331936A), urea derivatives (see JP 2003-168493A), sheet clay minerals (see US 2007/0275546A1), dibenzylidene D-sorbitol, cholesterol derivatives, amino acid derivatives, trans-(1R,2R)-1,2-cyclohexanediamine alkylamide derivatives, alkylurea derivatives, N-octyl-D-gluconamide benzoate, double-headed amino acid derivatives, quaternary ammonium derivatives, and so on.

When light (sunlight or ultraviolet, visible, or near infrared light equal to sunlight) enters the photoelectric conversion device of the invention, the dye 13 in the working electrode 10 absorbs the light, and the thus excited dye 13 injects electrons into the metal oxide semiconductor layer 12. The electrons move to the adjacent conductive layer 11B, passes through an outer circuit, and reach the counter electrode 20. On the other hand, the electrolyte in the electrolyte-containing layer 30 is oxidized to return (reduce) the dye 13 having been oxidized with the movement of electrons to the ground state. The thus oxidized electrolyte is reduced upon receipt of the electrons having reached the counter electrode 20. In this way, the electron movement between the working electrode 10 and the counter electrode 20 and the associated oxidation-reduction reaction in the electrolyte-containing layer 30 are repeated, whereby electrons move continuously to steadily perform photoelectric conversion.

The photoelectric conversion device of the invention is made, for example, as follows.

A working electrode 10 is provided. First of all, a metal oxide semiconductor layer 12 having a porous structure is formed on the side of the conductive layer 11B of the conductive substrate 11 by electrodeposition or firing. The electrodeposition is carried out by, for example, heating an electrolytic bath containing a metal salt providing a metal oxide semiconductor material to a predetermined temperature while bubbling with oxygen or air, immersing the conductive substrate 11 therein, and applying a given voltage between the substrate 11 and a counter electrode, thereby to deposit a metal oxide semiconductor material with a porous structure on the conductive layer 11B. The counter electrode may be moved appropriately in the electrolytic bath. The firing method is carried out by, for example, dispersing powder of a metal oxide semiconductor material in a medium, applying the resulting slurry to the conductive substrate 11, followed by drying, followed by firing to form a porous structure. Then a dye solution of a dye 13 containing the novel compound of the invention represented by general formula (1) in an organic solvent is prepared. The conductive substrate 11 having the metal oxide semiconductor layer 12 is immersed in the dye solution to fix the dye 13 onto the metal oxide semiconductor layer 12.

The concentration of the novel compound of the invention in the dye solution is preferably $1.0 \times 10^{-5}$ to $1.0 \times 10^{-3}$ mol/dm$^3$, more preferably $5.0 \times 10^{-5}$ to $5.0 \times 10^{-4}$ mol/dm$^3$. The organic solvent used to prepare the dye solution is not particularly limited as long as it is capable of dissolving the novel compound of the invention. Useful organic solvents include hydrocarbons, such as toluene, benzene, and xylene; alcohols, such as methanol, ethanol, and t-butanol: ether alcohols, such as methyl cellosolve, ethyl cellosolve, butyl cellosolve, and butyl diglycol; ketones, such as acetone, methyl ethyl ketone, methyl isobutyl ketone, cyclohexanone, and diacetone alcohol; esters, such as ethyl acetate, butyl acetate, and methoxyethyl acetate; acrylic esters, such as ethyl acrylate and butyl acrylate; fluoroalcohols, such as 2,2,3,3-tetrafluoropropanol; chlorinated hydrocarbons, such as methylene dichloride, dichloroethane, and chloroform; acetonitrile; and tetrahydrofuran. These organic solvents may be used in any combination thereof. Preferred solvents are toluene, acetonitrile, and alcohols, with acetonitrile and alcohols being more preferred.

An conductive layer 22 is then formed on one side of an conductive substrate 21 to make a counter electrode 20. The conductive layer 22 can be formed by, for example, sputtering an electroconductive material.

The working electrode 10 and the counter electrode 20 are put together with a predetermined space therebetween using a spacer (such as a sealant) such that the side of the dye 13 of the working electrode 10 and the side of the conductive layer 22 of the counter electrode 20 face each other, and the assembly is totally sealed while leaving an inlet for injecting an electrolyte. Subsequently, an electrolyte is injected through the inlet into the space between the working electrode 10 and the counter electrode 20, followed by sealing the inlet to form the electrolyte-containing layer 30. There is thus completed a photoelectric conversion device illustrated in FIGS. 1 and 2.

Since the dye 13 in the photoelectric conversion device of the invention contains the compound of the invention represented by general formula (1), the dye 13 is prevented from desorbing from the carrier (the metal oxide semiconductor layer 12) into the electrolyte-containing layer 30 compared with when other dye compounds are used. Because the amount of the dye 13 supported on the metal oxide semiconductor layer 12 does not decrease, the amount of electrons injected from the dye 13 to the metal oxide semiconductor layer 12 does not decrease. Through this effect, the photoelectric conversion device of the invention exhibits improved durability.

While the photoelectric conversion device has been described with particular reference to the configuration in which the electrolyte-containing layer 30 is provided between the working electrode 10 and the counter electrode 20, the electrolyte-containing layer 30 may be replaced with a solid charge transfer layer. In that case, the solid charge transfer layer has a solid material in which carrier transfer takes part in electric conduction. Such a material is preferably an electron transport material or a hole transport material.

Examples of the hole transport material include aromatic amines and triphenylene derivatives, such as oligothiophene compounds, polypyrrole, polyacetylene or its derivatives, poly(p-phenylene) or its derivatives, poly(p-phenylenevinylene) or its derivatives, polythienylenevinylene or its derivatives, polythiophene or its derivatives, polyaniline or its derivatives, polytoluidine or its derivatives, and like organic electroconductive polymers.

A p-type inorganic compound semiconductor may be used as the hole transport material. The p-type inorganic compound semiconductor preferably has a band gap of 2 eV or more, more preferably 2.5 eV or more. The ionization potential of the p-type inorganic compound semiconductor must be smaller than that of the working electrode 10 in order to secure the condition for reducing the positive holes of the dye. The ionization potential of the p-type inorganic compound semiconductor, while varying depending on the dye used, is preferably 4.5 to 5.5 eV, more preferably 4.7 to 5.3 eV.

Examples of the p-type inorganic compound semiconductor include compound semiconductors containing monovalent copper, such as CuI, CuSCN, CuInSe$_2$, Cu(In,Ga)Se$_2$, CuGaSe$_2$, Cu$_2$O, CuS, CuGaS$_2$, CuInS$_2$, and CuAlSe$_2$; GaP, NiO, CoO, FeO, Bi$_2$O$_3$, MoO$_2$, and Cr$_2$O$_3$.

The solid charge transfer layer may be formed directly on the working electrode 10, and then a counter electrode may be formed thereon.

The hole transport material including the organic photoconductive polymer may be introduced into the inside of the electrode by, for example, vacuum deposition, casting, coating, spin coating, dipping, electrolytic polymerization, or photoelectric polymerization. The hole transport material including the inorganic solid compound may be introduced into the inside of the electrode by, for example, casting, coating, spin coating, dipping, or electroplating. It is preferred that part of the thus formed solid charge transport layer, particularly a layer containing a hole transport material, partially penetrates the voids of the porous structure of the metal oxide semiconductor layer 12 to come into direct contact with the metal oxide semiconductor material.

The compound of the invention brings about improvement on conversion efficiency in an photoelectric conversion device having the solid charge transfer layer in place of the electrolyte-containing layer 30 similarly to the application to the photoelectric conversion device having the electrolyte-containing layer 30.

The applications of the photoelectric conversion device of the invention are not limited to the aforementioned solar cell and include, for example, photosensors.

EXAMPLES

The invention will now be illustrated in greater detail with reference to Examples of synthesis of the novel compounds of the invention and Examples and Comparative Examples of the carrier system (working electrode) having the compound synthesized in the Synthesis Example. It should be noted that the invention is not limited thereto.

In the following Synthesis Examples compound Nos. 1 to 4, 22, and 33 through 42 were synthesized. The carboxylic acid compounds and amine compounds used as precursors were purchased or synthesized by known processes.

Synthesis Example 1

Synthesis of Compound No. 1

A flask was charged with 100 mg (0.11 mmol) of MK-2 Dye (from Sigma-Aldrich), 0.1 ml of dimethylformamide, and 2 ml of chloroform, and 15 mg (0.12 mmol) of oxalyl chloride was added thereto, followed by stirring for 1 hour. At 0° C. 28 mg (0.12 mmol) of di-t-butyl iminodiacetate and 41 mg (0.31 mmol) of diisopropylethylamine were added thereto, followed by stirring for 1 hour. To the reaction mixture were added 10 ml of water and 10 ml of chloroform to conduct oil-water separation. The resulting organic layer was purified by silica gel column chromatography using chloroform as a mobile phase to give 30 mg (yield: 24%) of a purple solid. The solid was dissolved in 10 ml of dichloromethane, the solution was cooled to 0° C., and 9 mg (0.08 mmol) of trifluoroacetic acid was added thereto, followed by stirring for 1 hour. The temperature was elevated to room temperature, and the stirring was continued for 14 hours. The solvent was removed by evaporation, and the residue was purified by silica gel column chromatography using a 5:1 mixture of chloroform and methanol as a mobile phase to give 14 mg (52%) of a red solid, which was identified to be compound No. 1 by UV-VIS ($\lambda_{max}$), $^1$H-NMR, IR, TOF-MS. The analytical data obtained are given in Tables 1 through 4.

Synthesis Examples 2 to 15

Synthesis of Compound Nos. 2 to 4, 22, and 33 Through 42

Compound Nos. 2 to 4, 22, and 33 to 42 were synthesized in the same manner as in Synthesis Example 1, except for using carboxylic acid compounds and amine compounds corresponding to the desired products. Identification of the resulting compounds was done in the same manner as in Synthesis Example 1. The data obtained are shown in Tables 1 through 4.

TABLE 1

|  | Compound | Appearance | Yield (%) | $\lambda_{max}$ (nm) |
|---|---|---|---|---|
| Synthesis Example 1 | No. 1 | red solid | 52 | 487 (CHCl$_3$) |
| Synthesis Example 2 | No. 2 | red solid | 29 | 490 (CHCl$_3$) |
| Synthesis Example 3 | No. 3 | red solid | 40 | 495 (CHCl$_3$) |
| Synthesis Example 4 | No. 4 | yellow solid | 3 | 424 (CHCl$_3$) |
| Synthesis Example 5 | No. 22 | reddish purple solid | 78 | 489 (CHCl$_3$) |
| Synthesis Example 6 | No. 33 | reddish brown solid | 58 | 476 (CHCl$_3$) |
| Synthesis Example 7 | No. 34 | orange solid | 84 | 449 (CHCl$_3$) |
| Synthesis Example 8 | No. 35 | reddish purple solid | 77 | 489 (CHCl$_3$) |
| Synthesis Example 9 | No. 36 | reddish purple solid | 99 | 500 (CHCl$_3$) |
| Synthesis Example 10 | No. 37 | reddish purple solid | 57 | 499 (CHCl$_3$) |
| Synthesis Example 11 | No. 38 | reddish purple solid | 93 | 483 (CHCl$_3$) |
| Synthesis Example 12 | No. 39 | reddish purple solid | 20 | 514 (CHCl$_3$) |
| Synthesis Example 13 | No. 40 | reddish purple solid | 63 | 512 (CHCl$_3$) |
| Synthesis Example 14 | No. 41 | orange solid | 30 | 467 (CHCl$_3$) |
| Synthesis Example 15 | No. 42 | orange solid | 32 | 427 (CHCl$_3$) |

TABLE 2

| Compound | Solvent | $^1$H-NMR/Chemical shift (multiplicity, proton number) |
|---|---|---|
| No. 1 | CD$_3$OD | 8.26 (s, 1H), 8.09 (d, 1H), 8.06 (s, 1H), 7.89 (s, 1H), 7.67 (d, 1H), 7.50-7.42 (m, 3H), 7.24-7.18 (m, 2H), 7.03-6.92 (m, 3H), 4.41 (q, 2H), 4.25 (s, 2H), 4.14 (s, 2H), 2.87-2.71 (m, 8H), 1.80-1.63 (m, 8H), 1.62-1.23 (m, 27H), 0.91 (t, 12H) |
| No. 2 | CD$_3$OD | 8.21 (s, 1H), 8.09 (s, 1H), 8.07 (s, 1H), 8.63 (d, 1H), 7.49-7.40 (m, 3H), 7.22-.15 (m, 2H), 7.98-7.89 (m, 3H), 6.88 (t, 2H), 4.39 (q, 2H), 4.25-4.00 (m, 4H), 2.81-2.62 (m, 8H), 1.75-1.53 (m, 8H), 1.50-1.20 (m, 27H), 0.89 (t, 12H) |
| No. 3 | CDCl$_3$ | 8.39 (s, 1H), 8.28 (s, 1H), 8.12 (d, 1H), 8.11 (d, 2H), 7.67 (d, 1H), 7.50-7.33 (m, 6H), 7.16 (s, 1H), 6.98 (s, 1H), 6.96 (d, 2H), 4.61 (s, 2H), 4.34 (q, 2H), 2.84-2.72 (m, 8H), 1.78-1.59 (m, 8H), 1.48-1.21 (m, 27H), 0.88 (t, 12H) |
| No. 4 | CD$_3$OD | 8.37 (d, 1H), 8.10 (d, 2H), 7.74 (dd, 1H), 7.48-7.29 (m, 4H), 7.14 (dd, 1H), 4.36 (q, 2H), 4.11 (s, 2H), 4.02 (s, 2H), 2.76 (t, 2H), 1.62-1.56 (m, 2H), 1.38-1.19 (m, 9H), 0.79 (t, 3H) |

TABLE 2-continued

| Compound | Solvent | $^1$H-NMR/Chemical shift (multiplicity, proton number) |
|---|---|---|
| No. 22 | CDCl$_3$ | 8.31 (s, 1H), 8.29 (s, 1H), 8.16-8.11 (m, 3H), 7.69 (d, 1H), 7.47 (d, 1H), 7.39 (dd, 2H), 7.31 (d, 2H), 7.24 (dd, 1H), 7.17 (s, 1H), 7.03 (s, 1H), 6.99 (s, 1H), 6.96 (s, 1H), 4.36 (q, 2H), 3.88 (t, 2H), 2.78 (t, 8H), 2.34 (t, 2H), 1.78-1.53 (m, 12H), 1.50-1.19 (m, 39H), 0.89 (m, 12H). |
| No. 33 | CDCl$_3$ | 8.29 (s, 1H), 8.28 (s, 1H), 8.12 (d, 1H), 7.69 (d, 1H), 7.48 (dd, 1H), 7.40 (d, 1H), 7.37 (d, 1H), 7.25 (d, 1H), 7.20 (s, 1H), 7.08 (s, 1H), 4.56-4.18 (m, 6H), 2.86 (t, 2H), 2.77 (t, 2H), 1.79-1.60 (m, 4H), 1.50-1.13 (m, 15H), 0.89 (t, 6H) |
| No. 34 | CD$_3$OD | 8.17 (s, 1H), 7.97 (d, 1H), 7.90 (s, 1H), 7.53 (dd, 1H), 7.47 (s, 1H), 7.40-7.35 (m, 2H), 7.25 (d, 1H), 7.17 (s, 1H), 7.12 (dd, 1H), 4.38-4.32 (m, 2H), 4.23-4.15 (m, 4H), 2.53-2.46 (m, 4H), 1.56-1.45 (m, 4H), 1.28-1.10 (m, 15H), 0.81-0.72 (m, 6H) |
| No. 35 | CDCl$_3$ | 8.31 (s, 1H), 8.29 (s, 1H), 8.15-8.10 (m, 3H), 7.70 (d, 1H), 7.48 (d, 1H), 7.40 (dd, 2H), 7.32 (d, 2H), 7.25 (d, 1H), 7.18 (s, 1H), 7.04 (s, 1H), 6.99 (s, 1H), 6.96 (s, 1H), 4.37 (q, 2H), 3.91 (t, 2H), 2.79 (t, 8H), 2.35 (t, 2H), 1.82-1.20 (m, 41H), 0.89 (m, 12H). |
| No. 36 | CD$_3$OD | 8.13 (s, 1H), 8.07-8.00 (m, 3H), 7.76 (s, 1H), 7.55 (d, 1H), 7.46 (d, 2H), 7.36 (d, 1H), 7.23-7.14 (m, 3H), 7.06 (s, 1H), 6.77-6.69 (m, 3H), 4.34 (q, 2H), 4.03 (s, 2H), 3.99 (s, 2H), 3.71 (t, 2H), 2.70-2.50 (m, 8H), 2.43-2.27 (m, 4H), 1.70-1.18 (m, 41H), 0.99-0.80 (m, 12H) |
| No. 37 | CDCl$_3$ | 8.43 (s, 1H), 8.30 (s, 1H), 8.13 (d, 1H), 8.06 (d, 2H), 7.71 (d, 1H), 7.48 (d, 1H), 7.40 (dd, 2H), 7.30-7.22 (m, 3H), 7.19 (s, 1H), 7.17 (d, 2H), 7.06 (s, 1H), 6.99 (d, 2H), 6.92 (d, 2H), 4.37 (q, 2H), 3.97 (t, 2H), 2.80 (t, 8H), 2.41 (t, 2H), 1.95-1.52 (m, 12H), 1.48-1.24 (m, 29H), 0.90 (m, 12H). |
| No. 38 | CDCl$_3$ | 8.31 (s, 1H), 8.25 (s, 1H), 8.13 (d, 1H), 7.73 (d, 1H), 7.46 (dd, 1H), 7.40 (dd, 2H), 7.26 (dd, 1H), 7.19 (s, 1H), 7.01 (s, 1H), 7.00 (s, 1H), 4.42-4.16 (m, 8H), 3.95 (t, 2H), 2.89-2.78 (m, 6H), 1.83-1.63 (m, 10H), 1.55-1.22 (m, 37H), 0.97-0.82 (m, 15H) |
| No. 39 | CD$_3$OD | 8.29 (d, 1H), 8.11 (d, 1H), 8.01 (s, 1H), 7.70 (dd, 1H), 7.64 (s, 1H), 7.50-7.43 (m, 3H), .25 (s, 1H), 7.20 (dd, 1H), 7.11 (s, 1H), 7.01 (s, 1H) |
| No. 40 | CDCl$_3$ | 8.31 (s, 1H), 8.16 (s, 1H), 8.14 (d, 1H), 7.72 (d, 1H), 7.58 (s, 1H), 7.48 (dd, 1H), 7.43 (d, 1H), 7.41 (d, 1H), 7.25 (dd, 1H), 7.20 (s, 1H), 7.15 (s, 1H), 7.02 (s, 1H), 4.39 (q, 2H), 4.32 (t, 4H), 2.86-2.79 (m, 4H), 1.80-1.68 (m, 4H), 1.60-1.20 (m, 31H), 1.00-0.83 (m, 16H) |
| No. 41 | CD$_3$OD | 8.06 (s, 1H), 7.54 (d, 2H), 7.31-7.24 (m, 5H), 7.10-7.05 (m, 6H), 6.96 (d, 2H), 4.43-4.14 (m, 4H), 2.76 (t, 2H), 1.67-1.57 (m, 2H), 1.40-1.27 (m, 8H) 0.88 (t, 3H) |
| No. 42 | CD$_3$OD | 8.44 (s, 1H), 8.15 (d, 1H), 8.05 (s, 1H), 7.77 (t, 1H), 7.58-7.41 (m, 4H), 7.23 (t, 1H), 4.40 (q, 2H), 3.56 (s, 2H), 2.80 (t, 2H), 2.19 (t, 2H) 1.69-1.08 (m, 27H), 0.90 (t, 3H) |

TABLE 3

| Compound | IR/cm$^{-1}$ (KBr) |
|---|---|
| No. 1 | 3446, 3057, 2930, 2856, 2514, 2360, 2340, 2200, 1919, 1869, 1845, 1829, 1793, 1734, 1685, 1635, 1559, 1523, 1492, 1421, 1331, 1298, 1233, 1153, 1124, 1089 |
| No. 2 | 3020, 2360, 1869, 1845, 1829, 1771, 1717, 1697, 1653, 1636, 1603, 1558, 1520, 1507, 1490, 1457, 1417, 1379, 1313, 1215, 1124, 1038, 1015 |
| No. 3 | 3446, 2927, 2855, 2360, 2340, 2203, 1919, 1869, 1845, 1829, 1793, 1771, 1717, 1699, 1653, 1636, 1603, 1558, 1522, 1507, 1490, 1457, 1417, 1379, 1313, 1232, 1124, 1015 |
| No. 4 | 3420, 2925, 2853, 2360, 2340, 2206, 1869, 1845, 1829, 1793, 1771, 1717, 1699, 1684, 1670, 1653, 1635, 1577, 1559, 1541, 1521, 1507, 1490, 1473, 1457, 1419, 1396, 1339, 1234, 1091 |
| No. 22 | 2921, 2852, 2199, 1695, 1646, 1599, 1557, 1489, 1453, 1413, 1380, 1230, 1170, 1151, 1016 |
| No. 33 | 2923, 2853, 2198, 1725, 1625, 1597, 1558, 1487, 1409, 1329, 1230, 1190, 1151, 1123, 1087 |
| No. 34 | 2952, 2920, 2852, 2206, 1737, 1653, 1574, 1451, 1420, 1259, 1232, 1084, 1010 |
| No. 35 | 2954, 2919, 2855, 2198, 1687, 1602, 1595, 1454, 1422, 1382, 1233, 1157 |
| No. 36 | 2923, 2855, 2198, 1717, 1599, 1558, 1488, 1454, 1414, 1156 |
| No. 37 | 2953, 2920, 2852, 2196, 1700, 1646, 1600, 1557, 1508, 1485, 1416, 1317, 1233, 1197, 1168, 1107 |
| No. 38 | 2923, 2854, 2198, 1676, 1566, 1491, 1448, 1380, 1288, 1197, 1131, 1080 |
| No. 39 | 2952, 2853, 2197, 1724, 1627, 1598, 1568, 1489, 1406, 1317, 1293, 1230, 1201, 1151, 1133, 1006 |
| No. 40 | 2952, 2920, 2852, 2198, 1740, 1648, 1557, 1448, 1367, 1350, 1297, 1256, 1230, 1210, 1146, 1004 |
| No. 41 | 2926, 2855, 2202, 1726, 1638, 1560, 1491, 1416, 1324, 1281, 1212, 1178, 1019 |
| No. 42 | 2923, 2853, 2205, 1711, 1636, 1597, 1565, 1527, 1490, 1421, 1380, 1331, 1231, 1198, 1152, 1088 |

TABLE 4

| Example | Theoretical value | m/z |
|---|---|---|
| No. 1 | 1069.5 | 1069.5 (M+) |
| No. 2 | 1050.5 | 1050.6 (M+) |
| No. 3 | 1131.5 | 1131.5 (M+) |
| No. 4 | 571.2 | 571.2 (M+) |
| No. 22 | 1257.6 | 1257.6 (M+) |
| No. 33 | 737.3 | 737.4 (M+) |
| No. 34 | 697.2 | 697.2 (M+) |
| No. 35 | 1187.5 | 1187.4 (M+) |
| No. 36 | 1302.6 | 1302.7 (M+) |
| No. 37 | 1279.6 | 1279.6 (M+) |
| No. 38 | 1185.5 | 1185.4 (M+) |
| No. 39 | 1081.5 | 1081.4 (M+) |
| No. 40 | 1097.4 | 1097.4 (M+) |
| No. 41 | 621.2 | 621.4 (M+) |
| No. 42 | 697.4 | 697.5 (M+) |

Carrier systems of the invention were prepared using the compounds synthesized in accordance with the following procedure.

Example 1

Carrier System (Working Electrode) Using Compound No. 1

An electroconductive glass substrate 11 made of F—SnO$_2$ measuring 2.0 cm in length, 1.5 cm in width, and 1.1 mm in thickness was prepared. A 70 μm thick masking tape was stuck on the substrate 11 to surround a 0.5 cm-side square. A metal oxide slurry prepared by suspending titanium oxide powder (Ti-Nanoxide D, TiO$_2$ from Solaronix) in water in a concentration of 10 wt % was applied to the square to a uniform thickness and dried. After the masking tape was removed, the conductive substrate 11 was fired in an electric oven at 450° C. to form a metal oxide semiconductor layer 12 with a thickness of about 5 μm. Compound No. 1 was dissolved in toluene in a concentration of 3×10$^{-4}$ mol/dm$^3$ to prepare a dye solution. The conductive substrate 11 having the metal oxide semiconductor layer 12 was immersed in the dye solution to make a working electrode 10 having the dye 13 supported thereon. The resulting working electrode 10 was immersed in a removing liquid under conditions 1 or 2 below.

<Condition 1> removing liquid: acetonitrile, at 85° C. for 6 hours

<Condition 2> removing liquid: 0.5 M 4-t-butylpyridine acetonitrile:water (9:1 by volume), at 25° C. for 8 hours The ratio of the residual amount of the dye on the working electrode remaining after the immersion to the amount of the dye before the immersion, taken as 100, was regarded as a measure of resistance to desorption as calculated based on the absorption at the $\lambda_{max}$ of the dye. The results obtained are shown in Tables 5 and 6. The closer the ratio to 100, the higher the resistance to desorption. The absorptions at the $\lambda_{max}$ of the dye were obtained from the surface absorption spectra of the metal oxide semiconductor layer 12 of the working electrode 10 as determined by using a UV spectrometer (U3010 from Hitachi High-Technologies; slit width: 1 nm) in a measuring wavelength range of from 300 to 800 nm.

Examples 2 to 9 and Comparative Examples 1 and 2

A working electrode 10 was prepared in the same manner as in Example 1, except for replacing compound No. 1 with the compound shown in Tables 5 and 6. The resistance of the dye to desorption was determined in the same manner as in Example 1. The results obtained are shown in Tables 5 and 6.

TABLE 5

| <Condition 1> | | |
|---|---|---|
| | Compound | Resistance to desorption |
| Example 1 | No. 1 | 88 |
| Example 2 | No. 2 | 77 |
| Example 3 | No. 22 | 96 |
| Example 4 | No. 33 | 99 |
| Example 5 | No. 34 | 86 |
| Example 6 | No. 35 | 90 |
| Example 7 | No. 36 | 92 |
| Example 8 | No. 39 | 87 |
| Example 9 | No. 41 | 91 |
| Comparative example 1 | Comparative compound 1 | 44 |
| Comparative example 2 | Comparative compound 2 | 61 |

TABLE 6

| <Condition 2> | | |
|---|---|---|
| | Compound | Resistance to desorption |
| Example 1 | No. 1 | 93 |
| Example 2 | No. 2 | 80 |
| Example 3 | No. 22 | 99 |
| Example 6 | No. 35 | 81 |
| Example 7 | No. 36 | 91 |
| Example 8 | No. 39 | 79 |
| Comparative example 1 | Comparative compound 1 | 52 |
| Comparative example 2 | Comparative compound 2 | 60 |

[Chemical Formula 7]

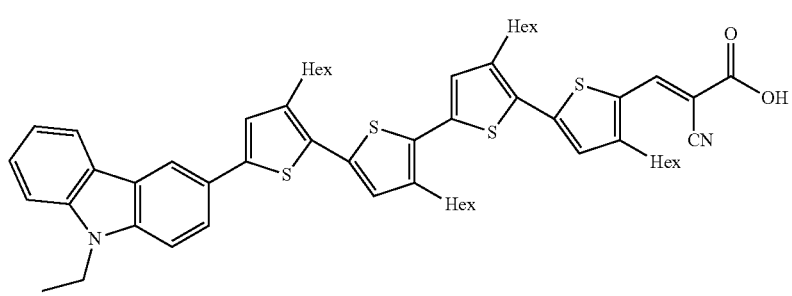

Comparative compound 1

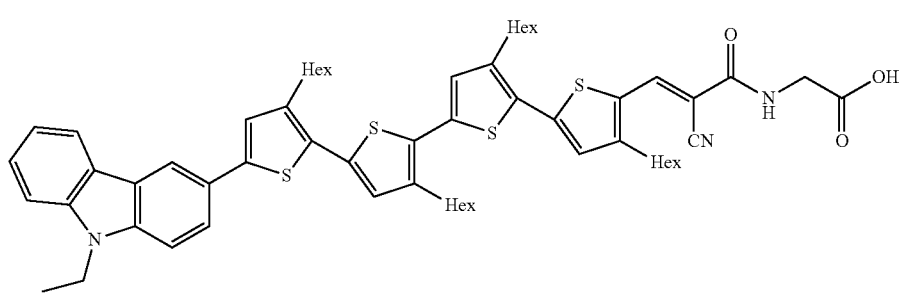

Comparative compound 2

As is proved by the results in Tables 5 and 6, the compounds of the invention represented by general formula (1) exhibit high durability against desorption from the carrier.

Examples of the photoelectric conversion device of the invention and the results of evaluation on their conversion efficiency are given below.

Examples 10 to 25 and Comparative Examples 3 and 4

As illustrated in FIG. 1, a carrier system (working electrode 10) which was prepared in the same manner as in Example 1 and a counter electrode 20 were assembled together with a 63 μm thick spacer therebetween to provide a space for an electrolyte-containing layer 30 therebetween and fixed by clips. The counter electrode was made by coating an ITO electrode (from Nishinoda Denko Co., Ltd.) as an conductive substrate 21 with graphite particles (conductive layer 22). An electrolyte solution prepared by dissolving 4-t-butylpyridine, lithium iodide, and iodine in acetonitrile in concentrations of 0.5 mol/dm$^3$, 0.5 mol/dm$^3$, and 0.05 mol/dm$^3$, respectively, was penetrated into the space to form an electrolyte-containing layer 30, thereby to make a photoelectric conversion device. The upper side of the cell was covered with a mask having an opening of 1 cm$^2$. The working electrode 10 and the counter electrode 20 were connected to the working electrode side and the counter electrode side of a potentiostat, and a short circuit current density (Jsc; unit: mA/cm$^2$) and an open circuit voltage (Voc; unit: V) were determined using Hyper-Monolight System SM-250 from Bunkoukeiki Co., Ltd., from which a conversion efficiency (%) of the photoelectric conversion device was calculated. The results obtained are shown in Table 7. In Examples 21 to 25 and Comparative Example 4 a ZnO electrode was used as a working electrode 10, which was made by using a slurry of zinc oxide powder (FINEX-50 from Sakai Chemical Industry Co., Ltd.; average particle size: 20 nm) in place of the slurry of titanium oxide powder.

TABLE 7

|  | Compound | Metal slurry | Conversion efficiency |
| --- | --- | --- | --- |
| Example 10 | No. 1 | TiO$_2$ | 3.3 |
| Example 11 | No. 3 | TiO$_2$ | 1.8 |
| Example 12 | No. 4 | TiO$_2$ | 1.9 |
| Example 13 | No. 22 | TiO$_2$ | 4.6 |
| Example 14 | No. 34 | TiO$_2$ | 2.3 |
| Example 15 | No. 35 | TiO$_2$ | 4.3 |
| Example 16 | No. 36 | TiO$_2$ | 3.0 |
| Example 17 | No. 38 | TiO$_2$ | 1.2 |

TABLE 7-continued

|  | Compound | Metal slurry | Conversion efficiency |
| --- | --- | --- | --- |
| Example 18 | No. 39 | TiO$_2$ | 3.5 |
| Example 19 | No. 40 | TiO$_2$ | 1.1 |
| Example 20 | No. 42 | TiO$_2$ | 2.0 |
| Comparative example 3 | Comparative compound 3 | TiO$_2$ | 0.1 |
| Example 21 | No. 1 | ZnO | 0.9 |
| Example 22 | No. 2 | ZnO | 0.7 |
| Example 23 | No. 3 | ZnO | 0.9 |
| Example 24 | No. 33 | ZnO | 0.9 |
| Example 25 | No. 41 | ZnO | 0.8 |
| Comparative example 4 | Comparative compound 1 | ZnO | 0.4 |

[Compound Formula 8]

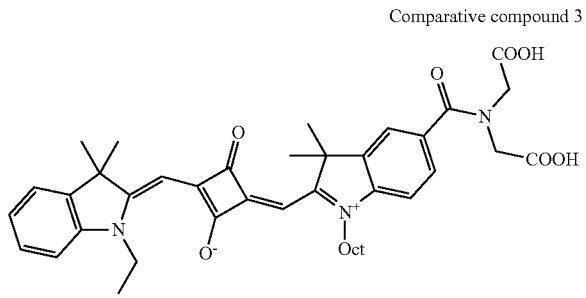

Comparative compound 3

The results of determining the conversion efficiency of the photoelectric conversion devices prove the following: Comparison between Examples 11 through 21 and Comparative Example 3, which are common in using a dicarboxylic acid compound, reveals that the novel compounds having the specific structure according to the invention provide high conversion efficiency. It is apparent from comparison between Examples 21 through 25 and Comparative Example 4 that the novel compounds of the invention provide high conversion efficiency.

As is apparent from the above results, the carrier system of the invention is useful because it is excellent in desorption resistance and light resistance and, when used in a photoelectric conversion device, achieves high conversion efficiency

The invention claimed is:

1. A novel compound represented by general formula (1):

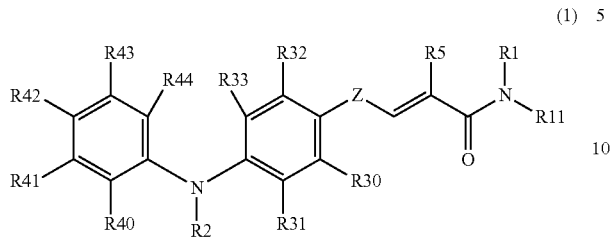

(1)

wherein Z represents a conjugated group having 1 to 50 carbon atoms selected from an unsaturated aliphatic hydrocarbon group, an aromatic hydrocarbon group, an aromatic heterocyclic group, and a group composed of one or more of these groups;
R1 represents an aromatic hydrocarbon group having 6 to 20 carbon atoms, an aromatic hydrocarbon group having 7 to 20 carbon atoms and substituted by an aliphatic hydrocarbon group, or an aliphatic hydrocarbon group having 1 to 20 carbon atoms, the aromatic hydrocarbon group having 6 to 20 carbon atoms, the substituted aromatic hydrocarbon group having 7 to 20 carbon. atoms, and the aliphatic hydrocarbon group being substituted by at least one of a carboxyl group, a cyano group, an amino group, an amide group, and a nitro group, the aliphatic hydrocarbon group being optionally interrupted by an interrupting group selected from —O—, —COO—, —OCO—, —NR²⁴—, —NR²⁴COO—, and —OCONR²⁴— at up to 3 positions and, upon the interruption occurring at 2 or 3 positions, the interrupting groups not being adjacent to each other; wherein R²⁴ an aromatic hydrocarbon group having 6 to 10 carbon atoms, an aromatic hydrocarbon group having 7 to 15 carbon atoms and substituted by an aliphatic hydrocarbon group, or an aliphatic hydrocarbon group having 1 to 10 carbon atoms, the aromatic hydrocarbon group having 6 to 10 carbon atoms, the substituted aromatic hydrocarbon group having 7 to 15 carbon atoms, and the aliphatic hydrocarbon group being optionally substituted with a carboxyl group, a cyano group, an amino group, an amide group, or a nitro group;
R2 represents a hydrogen atom or an optionally substituted hydrocarbon group having 1 to 20 carbon atoms;
R30, R31, R32, R33, R40, R41, R42, R43, and R44 each independently represent a hydrogen atom or an optionally substituted hydrocarbon group; R30 and R31, R40 and R41, R41 and R42, R42 and R43, or R33 and R44 being optionally connected to each other to form a ring;
R5 represents a hydrogen atom or a cyano group; and
R11 represents a group represented by structural formula (11-1) or(11-2):

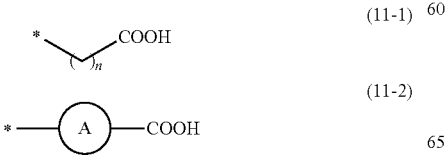

wherein n represents an integer of 1 to 4: ring A represents a benzene ring, a naphthalene ring, a cyclohexane ring, a cyclohexene ring, or a cyclohexadiene ring; the hydrogen atoms other than that of the carboxyl group in formulae (11-1) and (11-2) being optionally displaced by a carboxyl group, a cyano group, an amino group, an amide group, a nitro group, an aliphatic hydrocarbon group having 1 to 4 carbon atoms and substituted by at least one group selected from a carboxyl group, a cyano group, an amino group, an amide group and a nitro group, or an unsubstituted aliphatic hydrocarbon group having 1 to 4 carbon atoms.

2. The novel compound according to claim 1, being represented by general formula (2):

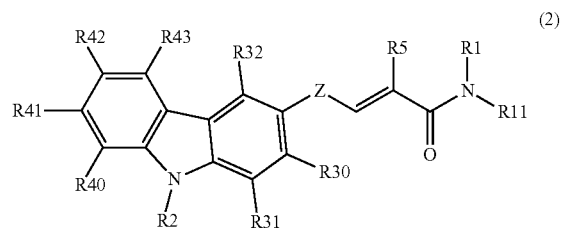

(2)

wherein. Z, R1,R11, R2, R30, R31, R32, R40, R41, R42, R3, and R5 are as defined for general formula (1).

3. The novel compound according to claim 2, wherein the conjugated group as represented by Z is a group composed of 1 to 7 groups linked to one another, the groups being selected from groups represented by formulae (Z-1) through (Z-10):

(Z-1)

(Z-2)

(Z-3)

(Z-4)

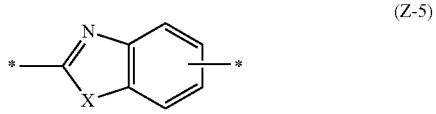

(Z-5)

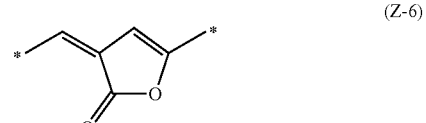

(Z-6)

(Z-7)

43

-continued

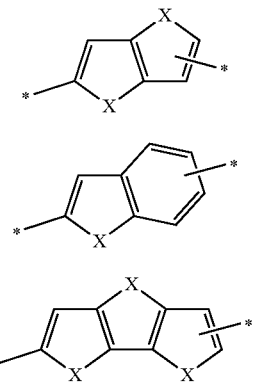

(Z-8)

(Z-9)

(Z-10)

wherein X represents S, O, NR6 or SiR6R7; the hydrogen atoms other than that directly bonded to the nitrogen atom is optionally displaced by a fluorine atom, a chlorine atom, an iodine atom, a cyano group, a nitro group, —OR6, —SR6, —NR6R7, —SiR6R7R8, or an optionally substituted aliphatic hydrocarbon group; R6, R7, and R8 each represent a hydrogen atom or an optionally substituted hydrocarbon group.

4. The noyel compound according to claim 2, wherein the conjuqated group as represented by Z has at least one group represented by formula (Z-7).

5. The novel compound according to claim 3, wherein the conjugated group as represented by Z has at least one group represented by formula (Z-7).

6. The novel compound according to claim 1, wherein the coniugated group as represented by Z is a group composed of 1 to 7 groups linked to one another, the groups being selected from groups represented by formulae (Z-1) through (Z-10):

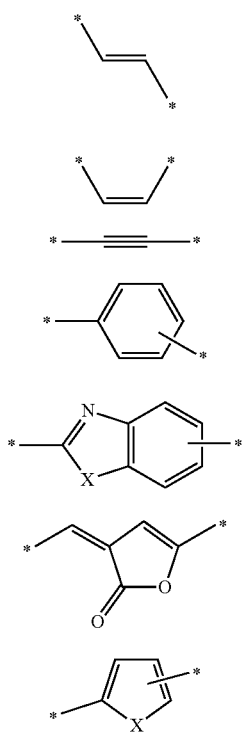

(Z-1)

(Z-2)

(Z-3)

(Z-4)

(Z-5)

(Z-6)

(Z-7)

44

-continued

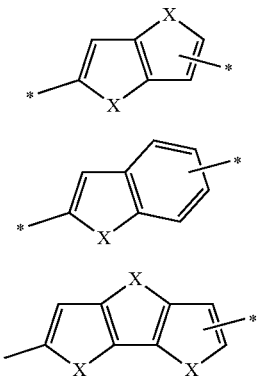

(Z-8)

(Z-9)

(Z-10)

wherein X represents S, O, NR6, or SiR6R7; the hydrogen atoms other than that directly bonded to the nitrogen atom is optionally displaced by a fluorine atom, a chlorine atom, an iodine atom, a cyano group, a nitro group, —OR6, —SR6, —NR6R7, —SiR6R7R8, or an optionally substituted aliphatic hydrocarbon group; R6, R7, and R8 each represent a hydrogen atom or an optionally substituted hydrocarbon group.

7. The novel compound according to claim 6, wherein the conjugated group as represented by Z has at least one group represented by formula (Z-7).

8. The novel compound according to claim 1, wherein the conjugated group as represented by Z has at least one group represented by formula (Z-7).

9. A carrier system comprising a carrier and a compound represented. by general formula (1) fixed to the carrier:

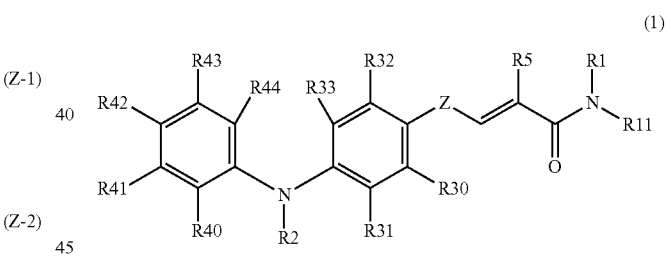

(1)

wherein Z represents a conjugated group having 1 to 50 carbon atoms selected from an unsaturated aliphatic hydrocarbon group, an aromatic hydrocarbon group, an aromatic heterocyclic group, and a group composed of one or more of these groups;

R1 represents an aromatic hydrocarbon group having 6 to 20 carbon atom, an aromatic hydrocarbon group having 7 to 20 carbon atoms and substituted by an aliphatic hydrocarbon group, or an aliphatic hydrocarbon group having 1 to 20 carbon atoms, the aromatic hydrocarbon group having 6 to 20 carbon atoms, the substituted aromatic hydrocarbon group having 7 to 20 carbon atoms, and the aliphatic hydrocarbon group being substituted by at least cue of a carboxyl group, a cyano group, an amino group, an amide group, and a nitro group, the aliphatic hydrocarbon qroup being optionally interrupted by an interrupting group selected from —O—, —COO—, —OCO—, —NR$^{24}$—, —NR$^{24}$COO—, and —OCONR$^{24}$— at lap to 3 positions and upon the interruption occurring at 2 or 3 positions, the interrupting groups not being adjacent to each other; wherein R$^{24}$ represents an aromatic hydrocarbon group having 6 to 10 carbon atoms, an aromatic hydrocarbon group having 7 to 15 carbon atoms and substituted by an aliphatic hydrocarbon group, or an aliphatic hydrocarbon group having 1 to 10 carbon atoms, the aromatic hydrocarbon group having 6 to 10 carbon atoms, the substituted aromatic hydrocarbon group having 7 to 15 carbon atoms, and the aliphatic hydrocarbon group being optionally substituted with a carboxyl group, a cyano group, an amino group, an amide group, or a nitro group;

R2 represents a hydrogen atom or an optionally substituted hydrocarbon group having 1 to 20 carbon atoms;

R30, R31, R32, R33, R40, R41, R42, R43, and R44 each independently represent a hydrogen atom or an optionally substituted hydrocarbon group; R30 and R31, R40 and R41, R41 and R42, R42 and R43, or R33 and R44 being optionally connected to form a ring;

R5 represents a hydrogen atom or a cyano group; and

R11 represents a group represented by structural formula (11-1) or (11-2):

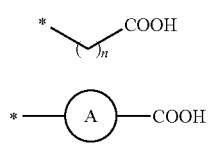

wherein n represents an integer 1 to 4; ring A represents a benzene ring, a naphthalene ring, a cyclohexane ring, a cyclohexene ring, or a cyclohexadiene ring; the hydrogen atoms other than that of the carboxyl group in formulae (11-1) and (11-2) being optionally displaced by a carboxyl group, a cyano group, an amino group, an amide group, a nitro group, an aliphatic hydrocarbon group having 1 to 4 carbon atoms and substituted by at least one group selected from a carboxyl group, a cyano group, an amino group, an amide group and a nitro group, or an unsubstituted aliphatic hydrocarbon group having 1 to 4 carbon atoms.

10. The carrier system according to claim 9, wherein the compound represented by general formula (1) is a compound represented by general formula (2):

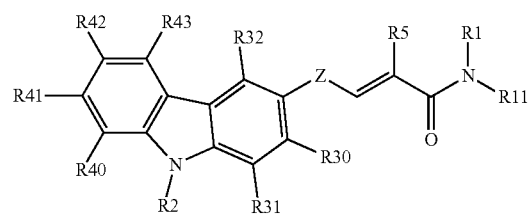

wherein Z, R1, R11, R2, R30, R31, R32, R40, R41), R42, R43, and R5 are as defined for general formula (1).

11. The carrier system according to claim 10, wherein the conjugated group as represented by Z is a group composed of 1 to 7 groups linked to one another, the groups being selected from groups represented by formulae (Z-1) through (Z-10):

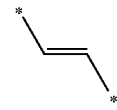

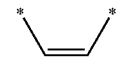

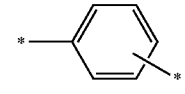

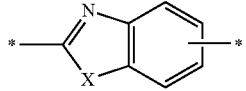

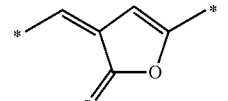

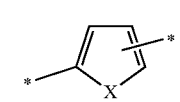

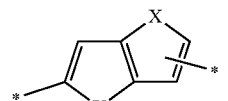

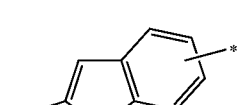

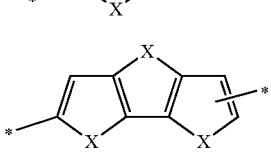

wherein X represents S, O, NR6, or SiR6R7; the hydrogen atoms other than that directly bonded to the nitrogen atom is optionally displaced by a fluorine atom, a chlorine atom, an iodine atom, a cyano group, a nitro group, —OR6, —SR6, —NR6R7, —SiR6R7R8, or an optionally substituted aliphatic hydrocarbon group; R6, R7, and R8 each represent a hydrogen atom or an optionally substituted hydrocarbon group.

12. The carrier system according to claim 10, wherein the conjugated group represented by Z has at least one group represented by formula (Z-7).

13. A photoelectric conversion device comprising an electrode having the carrier system according to claim 10.

14. The carrier system according to claim 11, wherein the conjugated group as represented by Z has at least one group represented by formula (Z-7).

15. The carrier system according to claim 9, wherein the conjugated group as represented by Z is a group composed of 1 to 7 groups linked to one another, the groups being selected from groups represented by formulae (Z-1) through (Z-10):

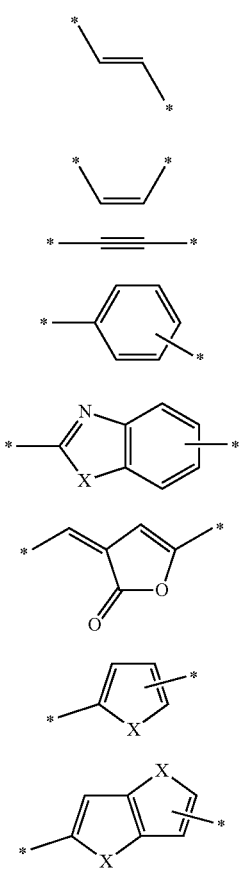

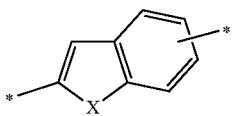

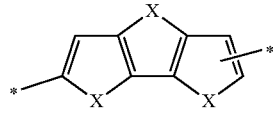

wherein X represents S, O, NR6, or SiR6R7; the hydrogen atoms other than that directly bonded to the nitrogen atom is optionally displaced by a fluorine atom, a chlorine atom, an iodine atom, a cyano group, a nitro group, OR6, —SR6, —NR6R7, —SiR6R7R8, or an optionally substituted aliphatic hydrocarbon group; R6, R7, and R8 each represent a hydrogen atom or an optionally substituted hydrocarbon group.

16. The carrier system according claim 15, wherein the conjugated group as represented by Z has at least one group represented by formula (Z-7).

17. A photoelectric conversion device comprising an electrode having the carrier system according to claim 15.

18. The carrier system according to claim 9, wherein the conjugated group as represented by Z has at least one qroup represented by formula (Z-7).

19. A photoelectric conversion device comprising an electrode having the carrier system according to claim 18.

20. A photoelectric conversion device comprising an electrode having the carrier system according to claim 9.

* * * * *